(12) United States Patent
Su et al.

(10) Patent No.: US 9,455,410 B2
(45) Date of Patent: Sep. 27, 2016

(54) MICROMOLECULAR ELECTRON TRANSPORT MATERIAL BASED ON PYRIDINE AND TRIAZOLE, PREPARATION METHOD AND ORGANIC LIGHT-EMITTING DIODE THEREOF

(71) Applicant: SHENZHEN CHINA STAR OPTOELECTRONICS TECHNOLOGY CO., LTD., Shenzhen (CN)

(72) Inventors: Shi-Jian Su, Shenzhen (CN); Hua Ye, Shenzhen (CN); Kunkun Liu, Shenzhen (CN); Xianglong Li, Shenzhen (CN); Yi-Fan Wang, Shenzhen (CN); Qinghua Zou, Shenzhen (CN)

(73) Assignee: SHENZHEN CHINA STAR OPTOELECTRONICS TECHNOLOGY CO., LTD, Shenzhen (CN)

( * ) Notice: Subject to any disclaimer, the term of this patent is extended or adjusted under 35 U.S.C. 154(b) by 381 days.

(21) Appl. No.: 14/235,802

(22) PCT Filed: Jan. 6, 2014

(86) PCT No.: PCT/CN2014/070166
§ 371 (c)(1),
(2) Date: Jan. 29, 2014

(87) PCT Pub. No.: WO2015/089919
PCT Pub. Date: Jun. 25, 2015

(65) Prior Publication Data
US 2015/0318485 A1    Nov. 5, 2015

(30) Foreign Application Priority Data

Dec. 20, 2013  (CN) .......................... 2013 1 0712330

(51) Int. Cl.
*H01L 51/00* (2006.01)
*C07D 401/14* (2006.01)
*C09K 11/06* (2006.01)
*H01L 51/50* (2006.01)

(52) U.S. Cl.
CPC ......... *H01L 51/0067* (2013.01); *C07D 401/14* (2013.01); *C09K 11/06* (2013.01); *H01L 51/5072* (2013.01)

(58) Field of Classification Search
None
See application file for complete search history.

(56) References Cited

U.S. PATENT DOCUMENTS

2010/0079066 A1    4/2010  Nomura
2014/0048787 A1    2/2014  Miki et al.

FOREIGN PATENT DOCUMENTS

CN    101253170 A    8/2008
CN    101665485 A    3/2010

*Primary Examiner* — J. L. Yang
(74) *Attorney, Agent, or Firm* — Mark M. Friedman

(57) ABSTRACT

The present invention provides a micromolecular electron transport material based on pyridine and triazole, which is represented by the formula I, and an organic light-emitting diode using the micromolecular electron transport material. The micromolecular electron transport material of the present invention can improve the capacity of electron injection, transmitting and hole-blocking, thus can gain high $E_T$ and reduce the driving voltage of device.

12 Claims, 14 Drawing Sheets

MICROMOLECULAR ELECTRON TRANSPORT MATERIAL BASED ON PYRIDINE AND TRIAZOLE, PREPARATION METHOD AND ORGANIC LIGHT-EMITTING DIODE THEREOF

FIELD OF THE INVENTION

The present invention relates to an organic light-emitting diode, especially relates to a micromolecular electron transport material based on triazole and pyridine, a preparation method and an organic light-emitting diode thereof.

BACKGROUND OF THE INVENTION

Researches of organic light-emitting diodes (OLED) have entered a stage of industrial application presently, research institutes, colleges and enterprises have invested lots of manpower, material resources and financial resources into related researches and applications. Besides of the research and development of light-emitting materials, the research and development of materials with efficient carrier transport function has become something of a hot topic. For now, most organic materials arranged in a p-type structure, which makes the mobility of holes in organic layers much higher than that of electrons and causes disequilibrium of carriers and inefficiency of devices. Therefore, it is urgent to research and develop electron transport materials.

Currently, efficient carrier transport materials are marked by some of the following features: (1) a deeper LUMO energy level, which leads to excellent characteristics of electron injection of the materials; (2) higher electron mobility; (3) a deeper HOMO energy level, which leads to an excellent hole-blocking ability of the materials; (4) a higher triplet energy level ($E_T$), which blocks diffusion of exciton. The widely used electron transport material TAZ (which is represented by the following formula II) cannot meet the above demands, this is because the LUMO energy level and the HOMO energy level of TAZ are −2.7 eV and −6.3 eV, wherein the LUMO energy level is so shallow that it will cause a higher electron injection barrier and a higher driving voltage of a device and is bad for industrialization. The lower electron mobility of TAZ (which is $10^{-6}$ cm$^2$V$^{-1}$S$^{-1}$) also restricts its application. In addition, the $E_T$ of TAZ is only 2.7 eV, which cannot block diffusion of exciton, because of the biphenyl group linking in para position consisted in its molecule.

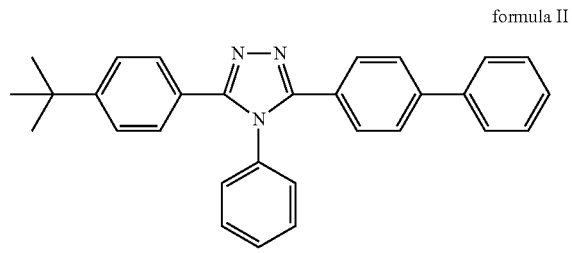 [SMILES: CC(C)(C)c1ccc(-c2nnc(-c3ccc(-c4ccccc4)cc3)n2-c2ccccc2)cc1]

formula II

In recent years, Su etc. have made a detailed and in-depth study on electron transport materials having pyridine groups which shows low LUMU energy level and high electron mobility due to the strong electrophilicity of pyridine. This promotes the development of electron transport materials and the industrialization of OLED greatly.

Based on the above considerations, it is necessary to provide a new electron transport material which can improve the capacity of electron injection, transmitting and hole-blocking, thus can gain high $E_T$ and reduce the driving voltage of device, so as to raise the potential of commercial application of electron transport materials.

SUMMARY OF THE INVENTION

The first object of the present invention is to provide a micromolecular electron transport material based on pyridine and triazole, which can improve the capacity of electron injection, transmitting and hole-blocking, thus can gain high $E_T$ and reduce the driving voltage of device.

To achieve the above object, the present invention provides a micromolecular electron transport material based on pyridine and triazole, which is contained in an electron transfer layer of an organic light emitting diode or a polymer light-emitting diode and is represented by the following formula I:

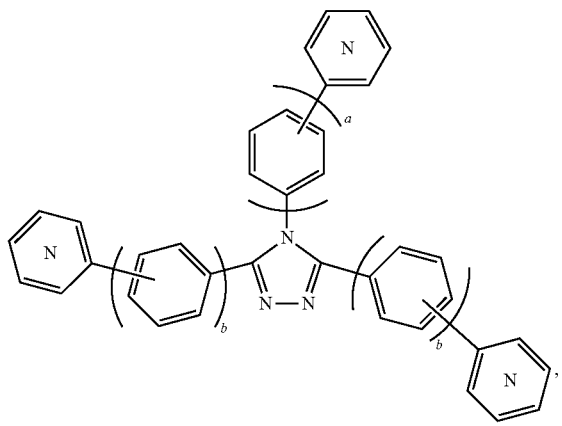

formula I wherein a and b are natural number greater than or equal to 1, respectively;

N is in ortho-, meta- or para-position of the pyridine ring in formula I; and benzene rings in formula I are connected on ortho-, meta- or para-position.

In one embodiment of the present invention, the micromolecular electron transport material is represented by the following formula i to iv:

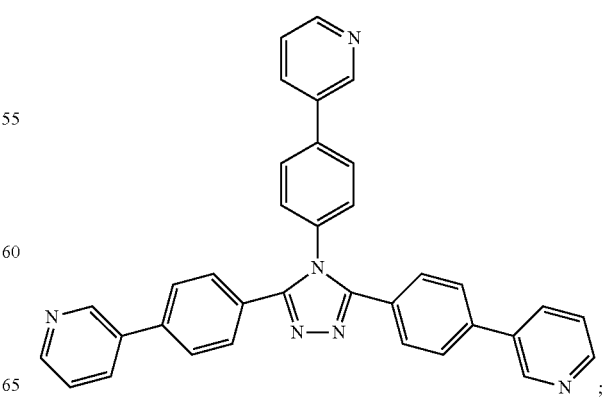

formula i

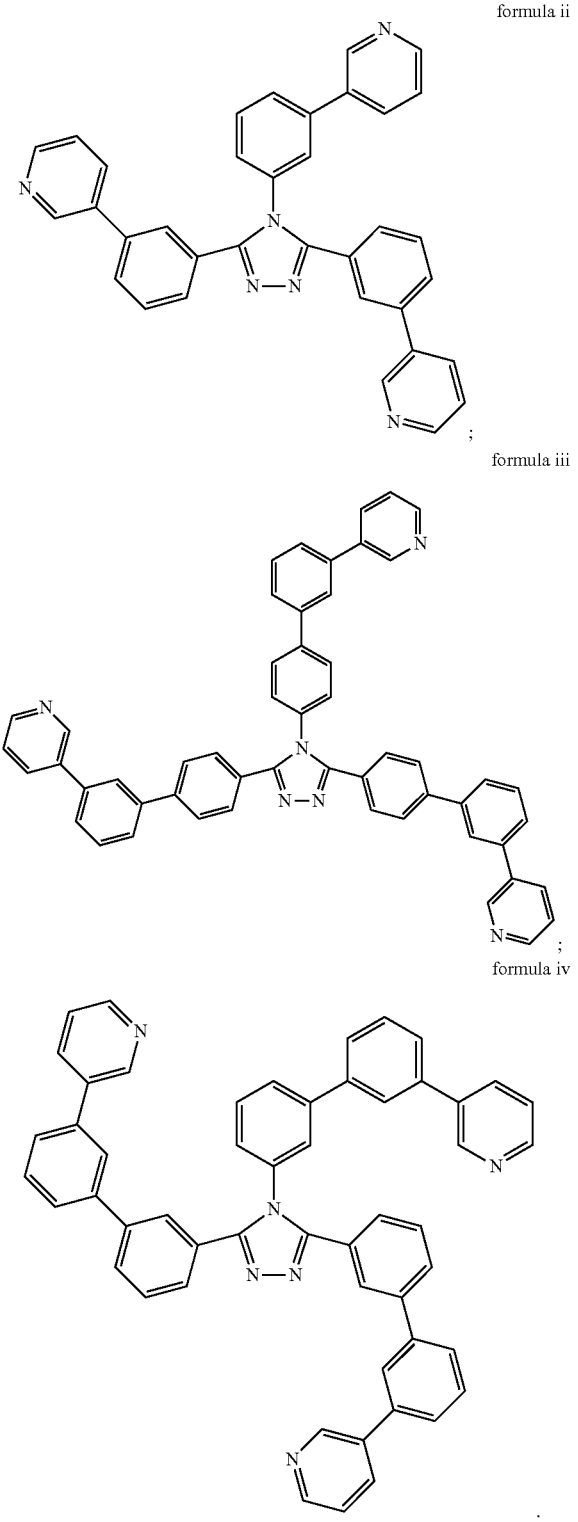

formula ii formula iii formula iv

The second object of the present invention is to provide a preparation method of the micromolecular electron transport material based on pyridine and triazole, which comprises the following steps of: (1) reacting a starting material A with hydrazine hydrate under the room temperature with N-methyl pyrrolidone as a solvent to synthesize product 1; (2) reacting the product 1 with phosphorus pentachloride under reflux with toluene as a solvent to synthesize product 2; (3) reacting the product 2 with N,N-dimethylaniline and a reactant B at a temperature of 135° C. to synthesize product 3; and (4) carrying out a Suzuki reaction occurs between the product 3 and a reactant C at a temperature of 95° C. to synthesize a target product;

Wherein the starting material A is selected from 4-bromobenzoyl chloride or 3-bromobenzoyl chloride, the reactant B is selected from 3-bromoaniline or 4-bromoaniline, and the reactant C is selected from 3-Pyridylboronic acid or 3-[3-(4,4,5,5-tetramethyl[1,3,2]dioxaborolan-2-yl)-phenyl]-pyridin.

In one embodiment of the present invention, the molar ratio of the starting material A to hydrazine hydrate is in a range of (1 to 3):1, and preferably is 2:1; the molar ratio of the product 1to phosphorus pentachloride is in a range of 1:(2 to 3), and preferably is 1:2.2; the molar ratio of the product 2 to N,N-dimethylaniline and the reactant B is in a range of 1:(40 to 80):1, and preferably is 1:60:1; and the molar ratio of the product 3 to the reactant C is in a range of 1:(3 to 5), and preferably is 1:3.5.

Certainly, some known purification steps are also included in the preparation method of the micromolecular electron transport material.

The third object of the present invention is to provide an organic light-emitting diode comprising: a substrate, a first electrode, a second electrode that faces the first electrode, a light-emitting layer that is sandwiched between the first electrode and the second electrode, and an electron transfer layer that is sandwiched between the light-emitting layer and the second electrode; wherein the electron transfer layer contains the above-mentioned micromolecular electron transport material based on pyridine and triazole.

In one embodiment of the present invention, the substrate is a transparent substrate.

It should be noted that all the compounds involved in the present invention are commercially available products unless stated.

Compared with the existing data and technology, the advantages and positive effects of the present invention are listed as follows:

(1) the preparation method of the micromolecular electron transport material containing pyridine and triazole of the present invention has fewer synthetic steps and is easy to carry out purification, which is conducive to industrial application;

(2) the micromolecular electron transport material containing pyridine and triazole of the present invention has better solubility, film-forming property and shape stability of film;

(3) the micromolecular electron transport material containing pyridine and triazole of the present invention has strong electrophilicity, low LUMU energy level and low energy barrier of electron injection due to the contained triazoles and pyridine rings; and (4) in the micromolecular electron transport material containing pyridine and triazole of the present invention, the pyridine rings and triazoles are connected by meta-benzene that performs poorer conjugation, which may maintain a higher triplet energy level of the materials effectually to block the migration of triplet excitons into the electron transfer layer.

11—a substrate of the organic light-emitting diode;

121—a first electrode of the organic light-emitting diode;

122—a second electrode of the organic light-emitting diode;

13—a light-emitting layer of the organic light-emitting diode;

14—an electron transfer layer of the organic light-emitting diode.

DESCRIPTION OF THE INVENTION

Embodiments, for purposes of explanation, are set forth in order to provide a thorough understanding of the present invention and not to limit the technical solution of the present invention. It will be appreciated by those skilled in the art that the structure and preparation method of the micromolecular electron transport material in the present invention are not limited to the following embodiments, and compounds that is in accordance with the above formulas and limitations of groups fall within the scope of the present invention.

EXAMPLE 1

The Preparation of the Micromolecular Electron Transport Material Represented by Formula i The example provides a micromolecular electron transport material based on pyridine and triazole, which is contained in an electron transfer layer of an organic light-emitting diode or a polymer light-emitting diode, wherein the micromolecular electron transport material is represented by the following formula i:

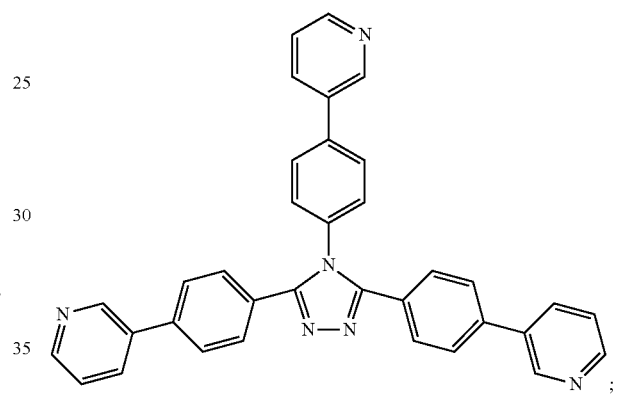

formula i and the synthetic route thereof is as follows.

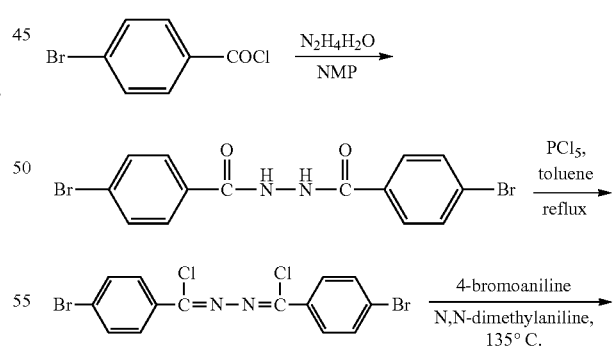

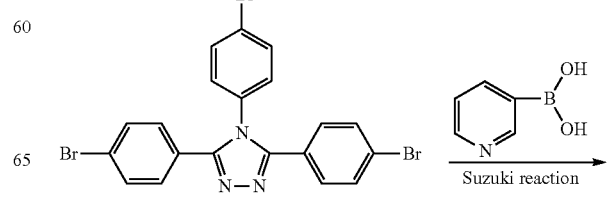

-continued

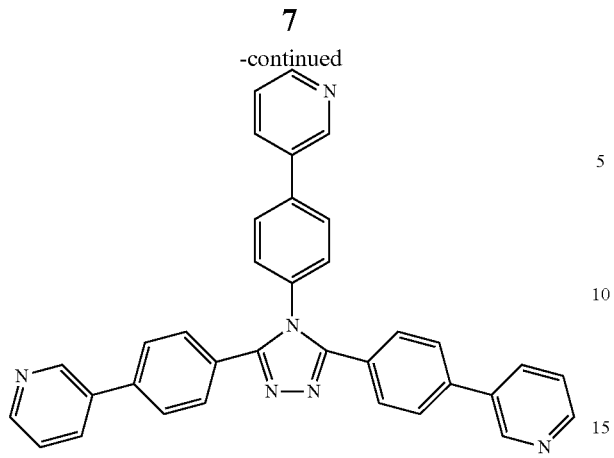

Figure 1:
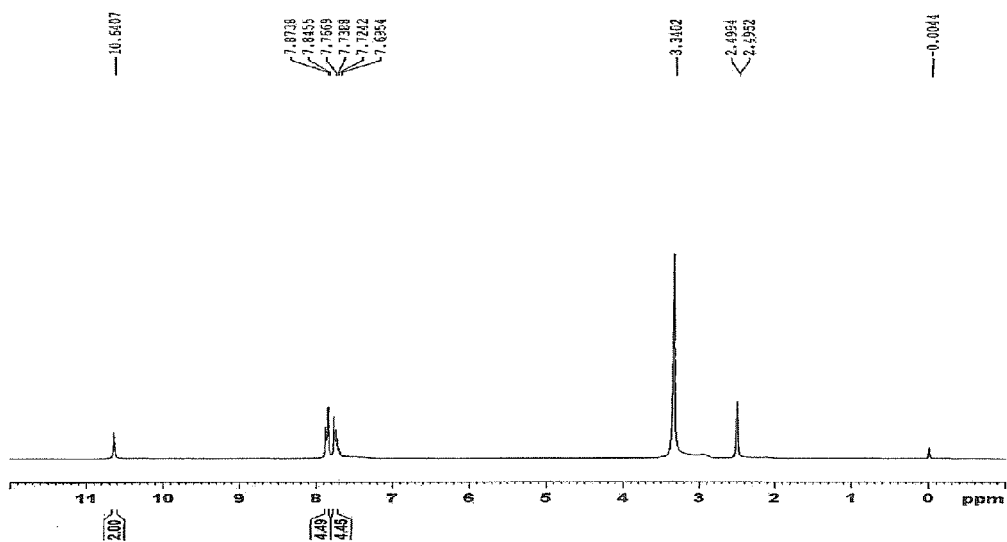
FIG. 1 is a spectrum that characterizes 1,2-bis(4-bromophenyl)hydrazine.

The preparation method thereof is described, as follows:

(1) Preparing 1,2-bis(4-bromophenyl)hydrazine p-Bromobenzoyl chloride (2.6 g, 12 mmol), 30 ml N-methyl pyrrolidone (NMP) are loaded into a 50 ml two-neck flask and stirred until completely dissolved. Then, hydrazine hydrate (0.30 g, 6 mmol) is dropped by injector and stirred until the next day at the room temperature. The reaction mixture is then poured into a beaker with 200 ml deionized water to separate out a large amount of white solid. The solid is suction filtrated and washed by deionized water, ethyl acetate and pure alcohol respectively, followed by vacuum drying to gain 1.83 g white solid, that is target product 1,2-bis(4-bromophenyl) hydrazine. The yield rate is 76.6% and the spectrum is seen in FIG. 1.

$^1$H NMR (300 MHz, DMSO-$d_6$, δ, ppm): 10.65 (s, 2H), 7.84 (d, 4H), 7.74 (d, 4H).

(2) Preparing 1,2-bis[chloro(4-bromophenyl)methylene]hydrazine

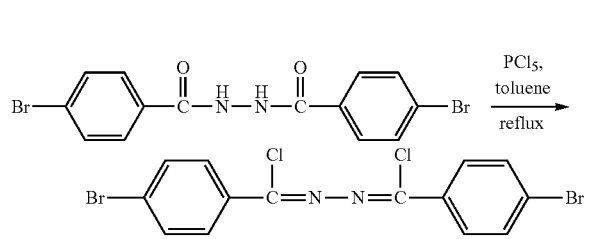

Figure 2:
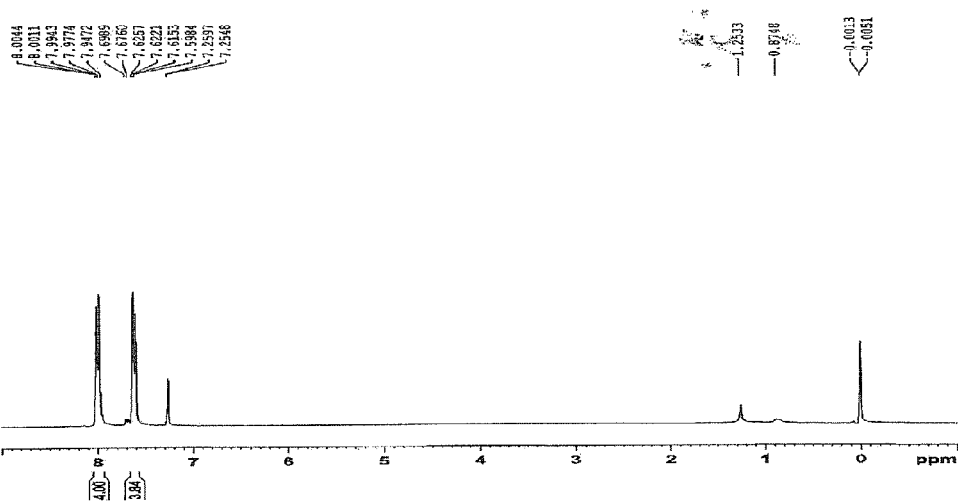
FIG. 2 is a spectrum that characterizes 1,2-bis[chloro(4-bromophenyl)methylene]hydrazine.

In the atmosphere of nitrogen, 1,2-bis(4-bromophenyl) hydrazine (0.84 g, 2.1 mmol), phosphorus pentachloride (0.96 g, 4.62 mmol) and 20 ml toluene are loaded into a 100 ml three-neck flask and stirred followed by refluxing for 5 hours. The reaction is quenched by water after being cooled down to the room temperature. Dichloromethane is added to attenuate and separate, and the aqueous phase obtained is extracted by dichloromethane for three times. The organic phase is merged and washed by saturated salt water for three times which is then dried by magnesium sulfate. The reaction system is suction filtrated, and the solvent of the filtrate obtained is removed under reduced pressure. After column separation, 0.73 g light yellow solid is gained, that is target product 1,2-bis[chloro(4-bromophenyl)methylene]hydrazine. The yield rate is 80.0% and the spectrum is seen in FIG. 2.

$^1$H NMR (300 MHz, CDCl3, δ, ppm): 8.00 (d, 4H), 7.60 (d, 4H).

(3) Preparing 3,4,5-tris(4-bromophenyl)-4H-1,2,4-triazole

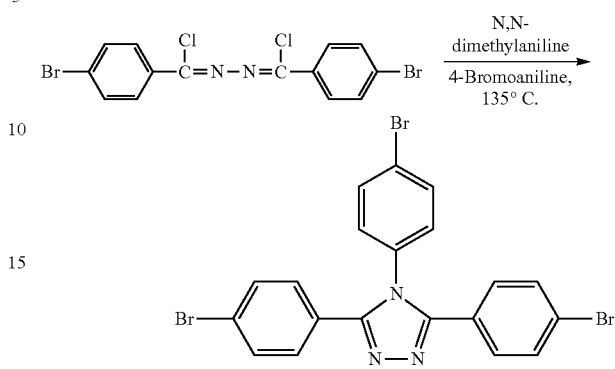

Figure 3:
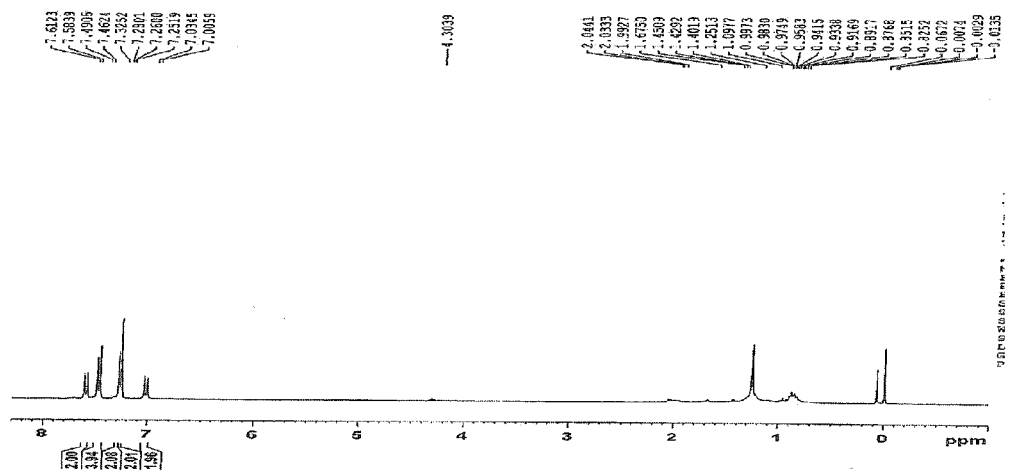
FIG. 3 is a spectrum that characterizes 3,4,5-tris(4-bromophenyl)-4H-1,2,4-triazole.

In the atmosphere of nitrogen, 1,2-bis[chloro(4-bromophenyl)methylene]hydrazine (0.86 g, 2.0 mmol), 4-bromoaniline (0.34 g, 2.0 mmol) and 15 ml N,N-dimethylaniline are loaded into a 100 ml three-neck flask and stirred followed by reacting for 12 hours at a temperature of 135° C. Cooling down to the room temperature, 30 ml HCl solution of 2 mol/L are added and stirred for 30 min followed by being suction filtrated, and the solid obtained is column separated to gain 0.63 g white solid, that is target product 3,4,5-tris(4-bromophenyl)-4H-1,2,4-triazole. The yield rate is 58.6% and the spectrum is seen in FIG. 3.

$^1$H NMR (300 MHz, CDCl$_3$, δ, ppm): 7.60 (d, 2H), 7.49 (d, 4H), 7.25 (d, 4H), 7.02 (d, 2H). $^{13}$C NMR (75 MHz, CDCl$_3$, δ, ppm): 153.94, 133.68, 133.61, 131.95, 130.19, 129.16, 125.30, 124.71, 124.25.

(4) Preparing 3,4,5-tris(4-(3-pyridyl)-phenyl)-4H-1,2,4-triazole (TPyTAZp) Represented by Formula i

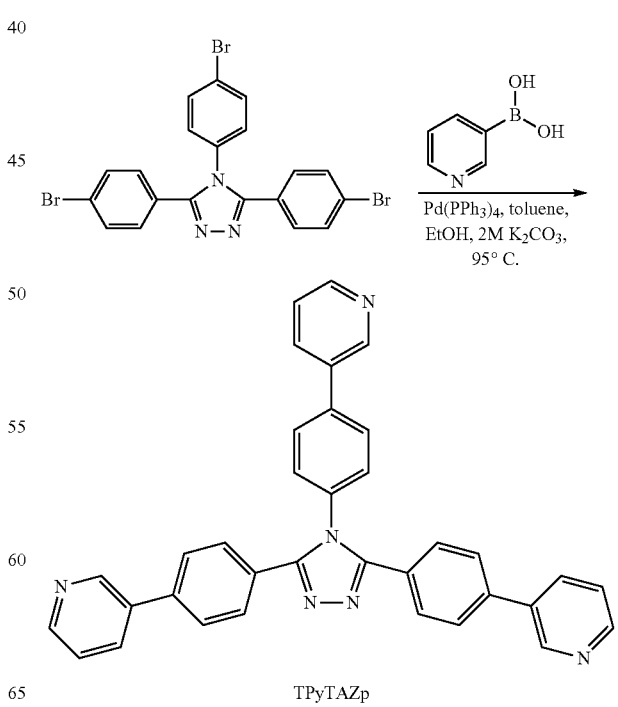

Figure 4A:
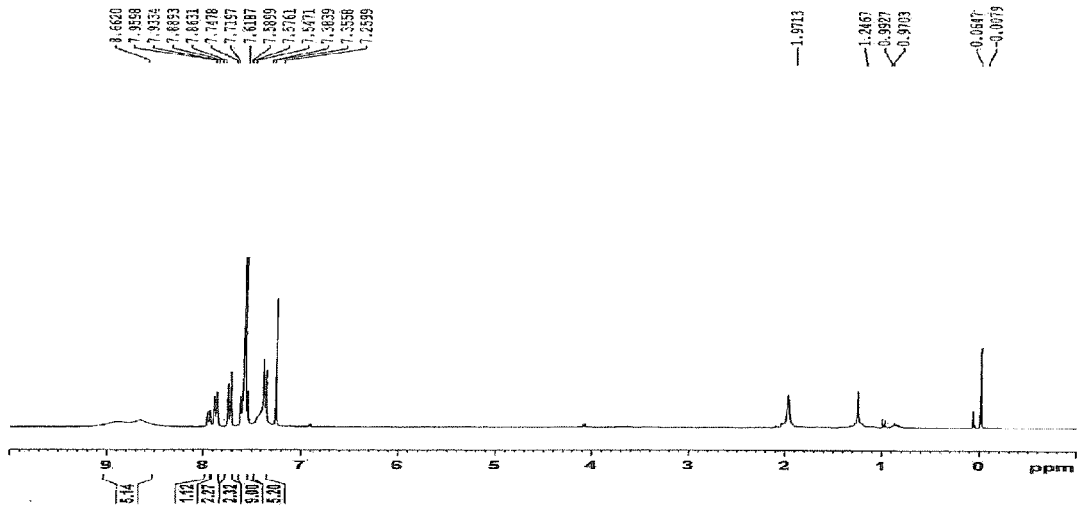
FIG. 4a to 4c are spectrums that characterize 3,4,5-tris(4-(3-pyridyl)-phenyl)-4H-1,2,4-triazole (TPyTAZp)
Figure 4B:
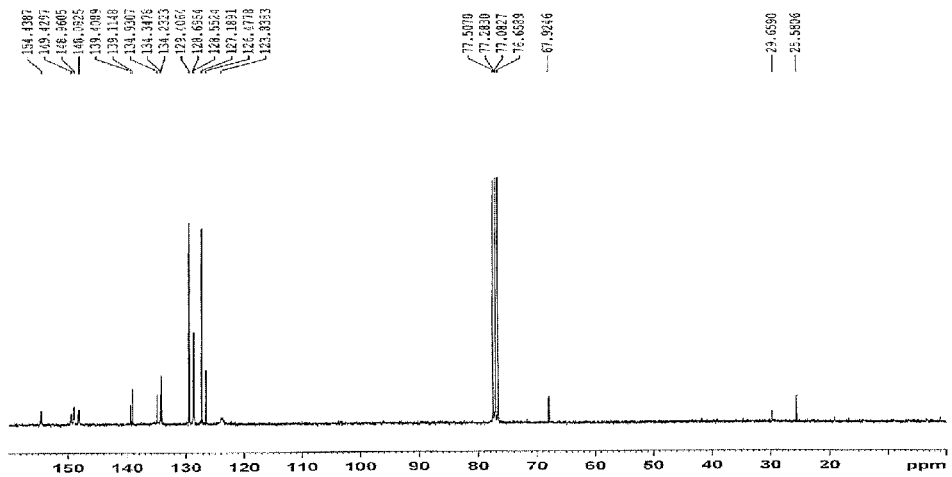
Figure 4C:
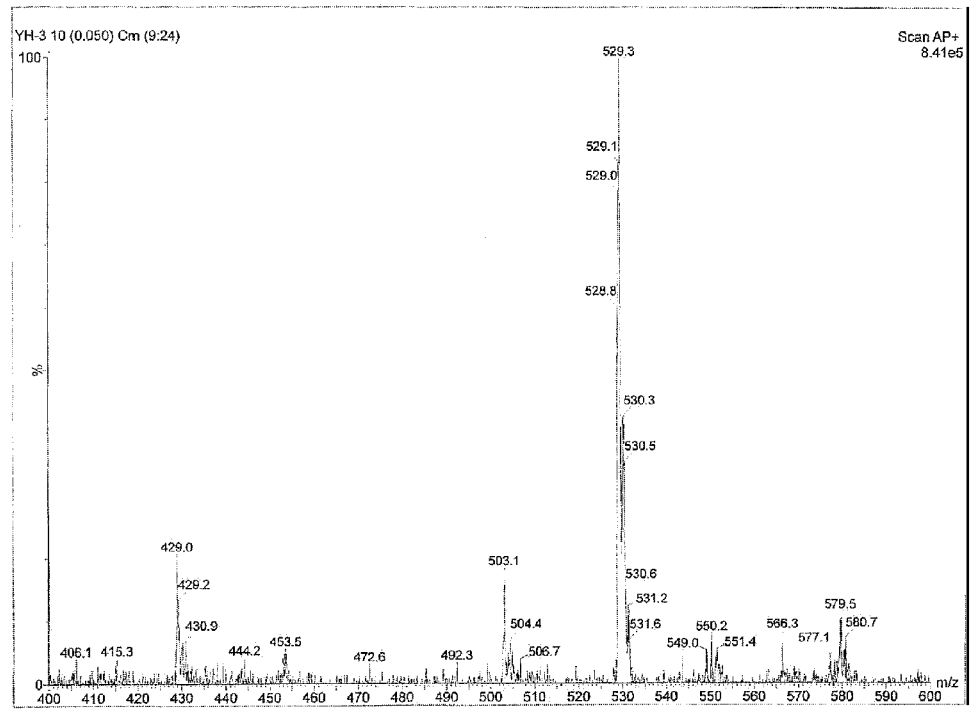

In the atmosphere of argon, 3,4,5-tris(4-bromophenyl)-4H-1,2,4-triazole (1.10 g, 2.1 mmol), 3-pyridylboronic acid (1.08 g, 8.64 mmol), 50 ml toluene, 20 ml ethanol, 20 ml potassium carbonate solution of 2 mol/L and tetrakis (triphenylphosphine) palladium (84 mg, 0.073 mmol) as a catalyst are loaded into a 250 ml three-neck flask and stirred followed by reacting for 24 hours at a temperature of 95° C. The reaction is quenched by water after being cooled down to the room temperature. Dichloromethane is added to attenuate and separate, and the aqueous phase obtained is extracted by dichloromethane for three times. The organic phase is merged and washed by saturated salt water for three times which is then dried by magnesium sulfate. The reaction system is suction filtrated, and the solvent of the filtrate obtained is removed under reduced pressure. After column separation, 0.94 g white solid is gained, that is target product TPyTAZp. The yield rate is 94.7% and the spectrum is seen in FIG. 4a to FIG. 4c.

$^1$H NMR (300 MHz, CDCl$_3$, δ, ppm): 9.10-8.47 (m, 5H), 7.96 (d, 1H), 7.88 (d, 2H), 7.73 (d, 2H), 7.62-7.52 (m, 9H), 7.48-7.30 (m, 5H). $^{13}$C NMR (75 MHz, CDCl$_3$, δ, ppm): 154.44, 149.43, 148.96, 148.08, 139.41, 139.11, 134.93, 134.35, 134.23, 129.41, 128.70, 128.55, 127.19, 126.48, 123.84. Calcd C$_{35}$H$_{24}$N$_6$ 528.6, APCI$^+$-MS (m/z): 529.3 (M$^+$).

EXAMPLE 2

The Preparation of the Micromolecular Electron Transport Material Represented by Formula ii The example provides a micromolecular electron transport material based on pyridine and triazole, which is contained in an electron transfer layer of an organic light-emitting diode or a polymer light-emitting diode, wherein the micromolecular electron transport material is represented by the following formula ii:

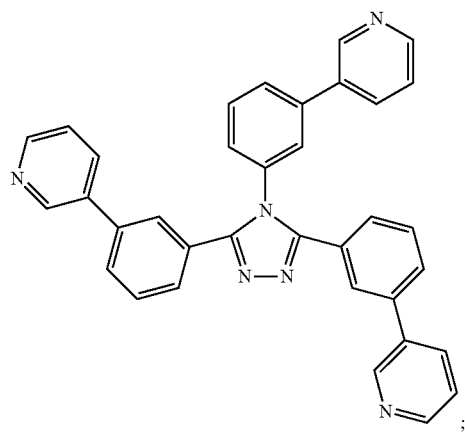

formula ii and the synthetic route thereof is as follows.

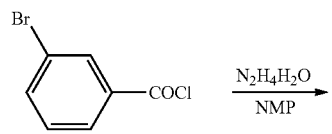

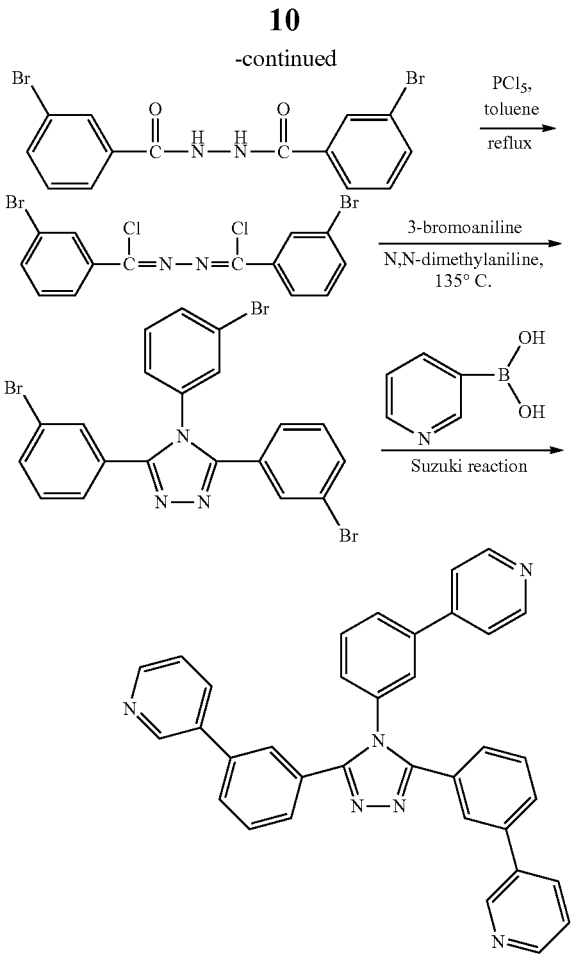

Figure 5:
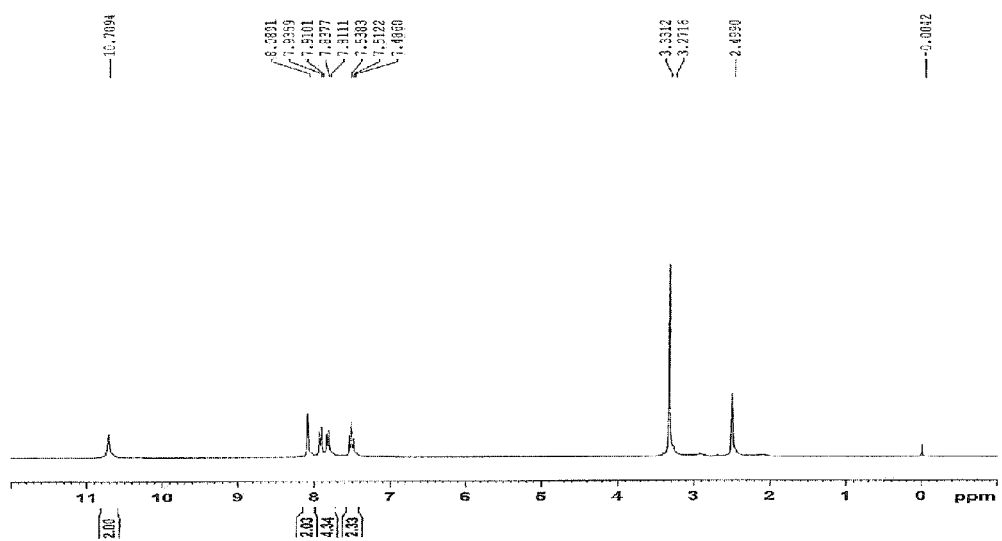
FIG. 5 is a spectrum that characterizes 1,2-bis(3-bromophenyl)hydrazine.

The preparation method thereof is described, as follows:

(1) Preparing 1,2-bis(3-bromophenyl)hydrazine 3-bromobenzoyl chloride (2.6 g, 12 mmol), 30 ml N-methyl pyrrolidone (NMP) are loaded into a 50 ml two-neck flask and stirred until completely dissolved. Then, hydrazine hydrate (0.30 g, 6 mmol) is dropped by injector and stirred until the next day at the room temperature. The reaction mixture is then poured into a beaker with 200 ml deionized water to separate out a large amount of white solid. The solid is suction filtrated and washed by deionized water, ethyl acetate and pure alcohol respectively, followed by vacuum drying to gain 1.80 g white solid, that is target product 1,2-bis(3-bromophenyl)hydrazine. The yield rate is 75.3% and the spectrum is seen in FIG. 5.

$^1$H NMR (300 MHz, DMSO-d$_6$, δ, ppm): 10.71 (s, 2H), 8.09 (s, 2H), 7.92 (d, 2H), 7.82 (d, 2H), 7.51 (t, 2H).

(2) Preparing 1,2-bis[chloro(3-bromophenyl)methylene]hydrazine

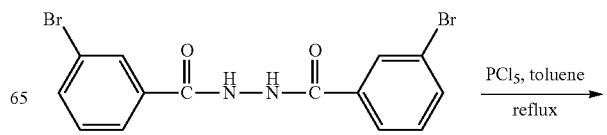

-continued

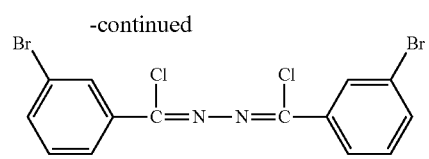

Figure 6:
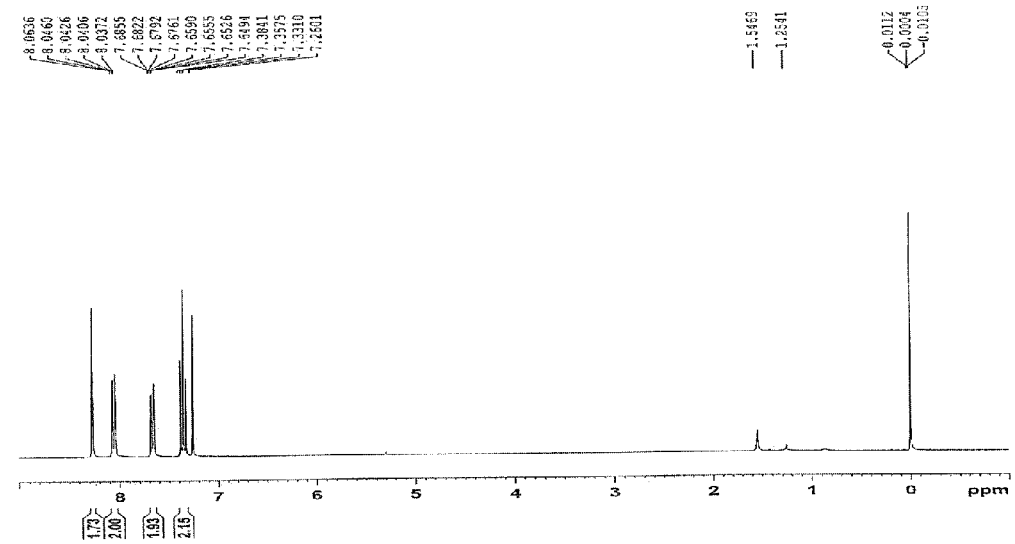
FIG. 6 is a spectrum that characterizes 1,2-bis[chloro(3-bromophenyl)methylene]hydrazine.

In the atmosphere of nitrogen, 1,2-bis(3-bromophenyl) hydrazine (3.60 g, 9.0 mmol), phosphorus pentachloride (7.50 g, 36.0 mmol) and 43 ml toluene are loaded into a 100 ml three-neck flask and stirred followed by refluxing for 12 hours. The reaction is quenched by saturated solution of sodium hydroxide after being cooled down to the room temperature. Dichloromethane is added to attenuate and separate, and the aqueous phase obtained is extracted by dichloromethane for three times. The organic phase is merged and washed by deionized water for three times which is then dried by magnesium sulfate. The reaction system is suction filtrated, and the solvent of the filtrate obtained is removed under reduced pressure. After column separation, 3.80 g light yellow solid is gained, that is target product 1,2-bis[chloro(3-bromophenyl)methylene]hydrazine. The yield rate is 98.3% and the spectrum is seen in FIG. 6. $^1$H NMR (300 MHz, CDCl$_3$, δ, ppm): 8.27 (s, 2H), 8.06 (d, 2H), 7.67 (d, 2H), 7.36 (t, 2H).

(3) Preparing 3,4,5-tris(3-bromophenyl)-4H-1,2,4-triazole

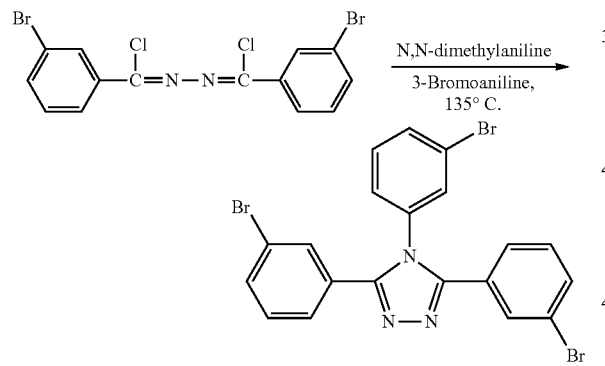

Figure 7A:
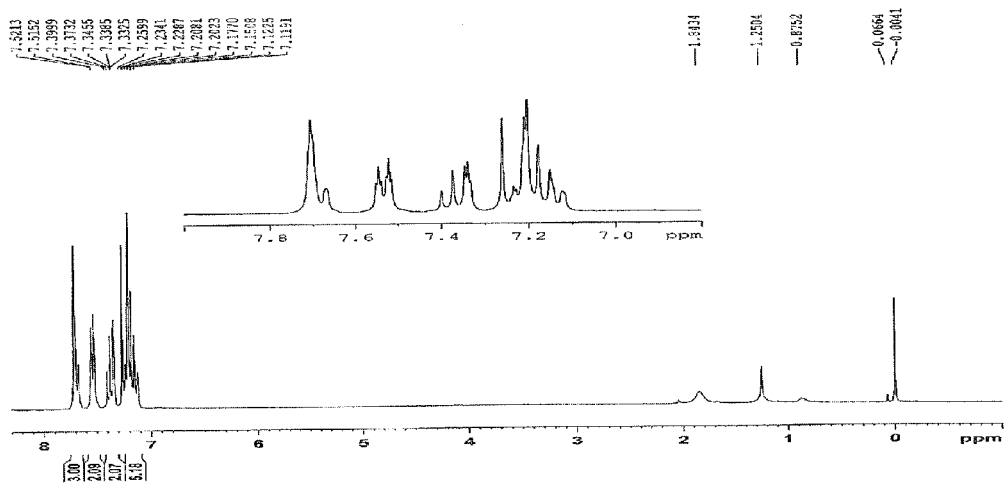
FIGS. 7a and 7b are spectrums that characterize 3,4,5-tris(3-bromophenyl)-4H-1,2,4-triazole.
Figure 7B:
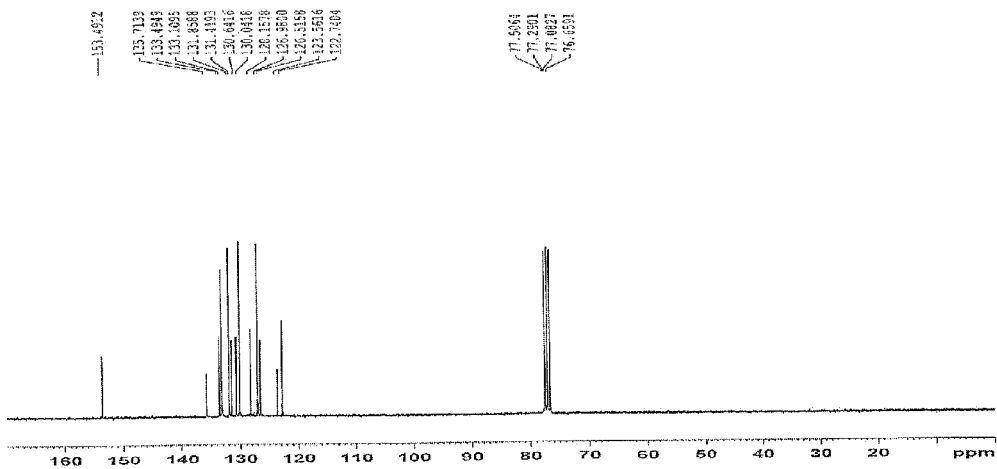

In the atmosphere of nitrogen, 1,2-bis[chloro(3-bromophenyl)methylene]hydrazine (3.44 g, 8.0 mmol), 3-bromoaniline (2.90 g, 16.8 mmol) and 60 ml N,N-dimethylaniline are loaded into a 100 ml three-neck flask and stirred followed by reacting for 12 hours at a temperature of 135° C. Cooling down to the room temperature, 120 ml HCl solution of 2 mol/L are added and stirred for 30 min. Dichloromethane is added to attenuate and separate, and the aqueous phase obtained is extracted by dichloromethane for three times. The organic phase is merged and washed by saline solutions for three times which is then dried by magnesium sulfate. The reaction system is suction filtrated, and the solvent of the filtrate obtained is removed under reduced pressure. After column separation, 3.16 g lightyellow solid is gained, that is target product 3,4,5-tris(3-bromophenyl)-4H-1,2,4-triazole. The yield rate is 77.5% and the spectrum is seen in FIG. 7a and FIG. 7b.

$^1$H NMR (300 MHz, CDCl$_3$, δ, ppm): 7.80 (s, 3H), 7.53 (d, 2H), 7.41-7.32 (m, 2H), 7.30-7.11 (m, 5H). $^{13}$C NMR (75 MHz, CDCl$_3$, δ, ppm): 153.49, 135.71, 133.49, 133.11, 131.86, 131.45, 130.64, 130.04, 128.16, 126.98, 126.52, 123.56, 122.74.

(4) Preparing 3,4,5-tris(3-(3-pyridyl)-phenyl)-4H-1,2,4-triazole (TPyTAZm) Represented by Formula ii

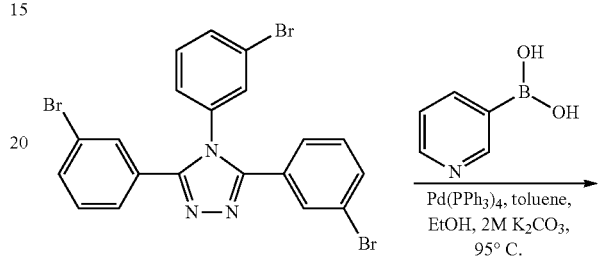

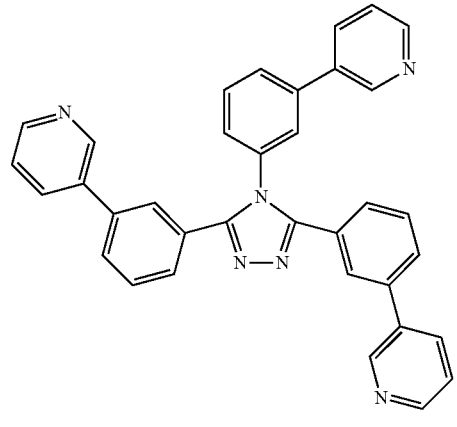

TPyTAZm

Figures 8A, 8B:
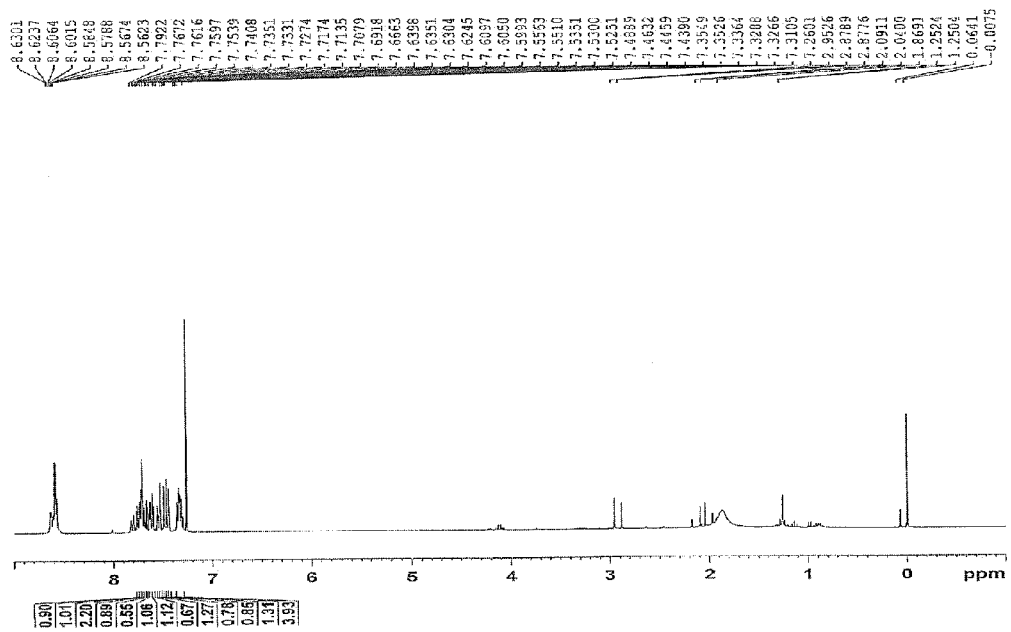
FIGS. 8a and 8b are spectrums that characterize 3,4,5-tris(3-(3-pyridyl)-phenyl)-4H-1,2,4-triazole (TPyTAZm)

In the atmosphere of argon, 3,4,5-tris(3-bromophenyl)-4H-1,2,4-triazole (0.267 g, 0.50 mmol), 3-pyridylboronic acid (0.223 g, 1.80 mmol), 25 ml toluene, 5 ml ethanol, 5 ml potassium carbonate solution of 2 mol/L and tetrakis (triphenylphosphine) palladium (35 mg, 0.030 mmol) as a catalyst are loaded into a 50 ml three-neck flask and stirred followed by reacting for 24 hours at a temperature of 95° C. The reaction is quenched by water after being cooled down to the room temperature. Dichloromethane is added to attenuate and separate, and the aqueous phase obtained is extracted by dichloromethane for three times. The organic phase is merged and washed by saturated salt water for three times which is then dried by magnesium sulfate. The reaction system is suction filtrated, and the solvent of the filtrate obtained is removed under reduced pressure. After column separation, 0.23 g white solid is gained, that is target product TPyTAZm. The yield rate is 87.1% and the spectrum is seen in FIGS. 8a and 8b.

$^1$H NMR (300 MHz, CDCl$_3$, δ, ppm): 8.64-8.55 (m, 6H), 7.82-7.78 (d, 1H), 7.76 (t, 1H), 7.74 (t, 1H), 7.73-7.70 (m, 2H), 7.69 (s, 1H), 7.67 (s, 1H), 7.65-7.62 (m, 1H), 7.60 (t, 1H), 7.56 (t, 1H), 7.53 (m, 1H), 7.49 (s, 1H), 7.46 (s, 1H), 7.45-7.43 (m, 1H), 7.37-7.30 (m, 4H). Calcd C$_{35}$H$_{24}$N$_6$ 528.6, APCI$^+$-MS (m/z): 529.2 (M$^+$).

EXAMPLE 3

The Preparation of the Micromolecular Electron Transport Material Represented by Formula iii The example provides a micromolecular electron transport material based on pyridine and triazole, which is contained in an electron transfer layer of an organic light-emitting diode or a polymer light-emitting diode, wherein the micromolecular electron transport material is represented by the following formula iii:

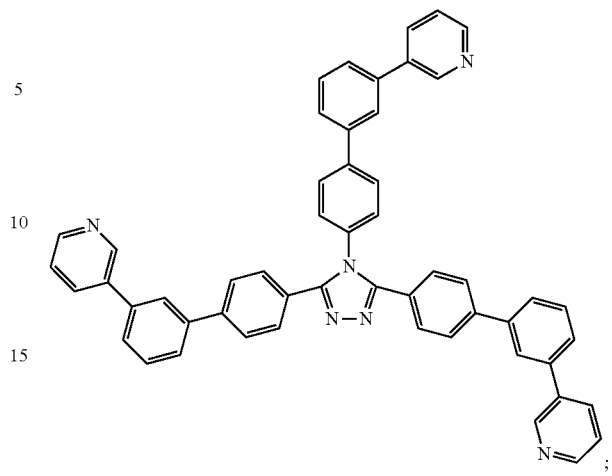

and the synthetic route thereof is as follows.

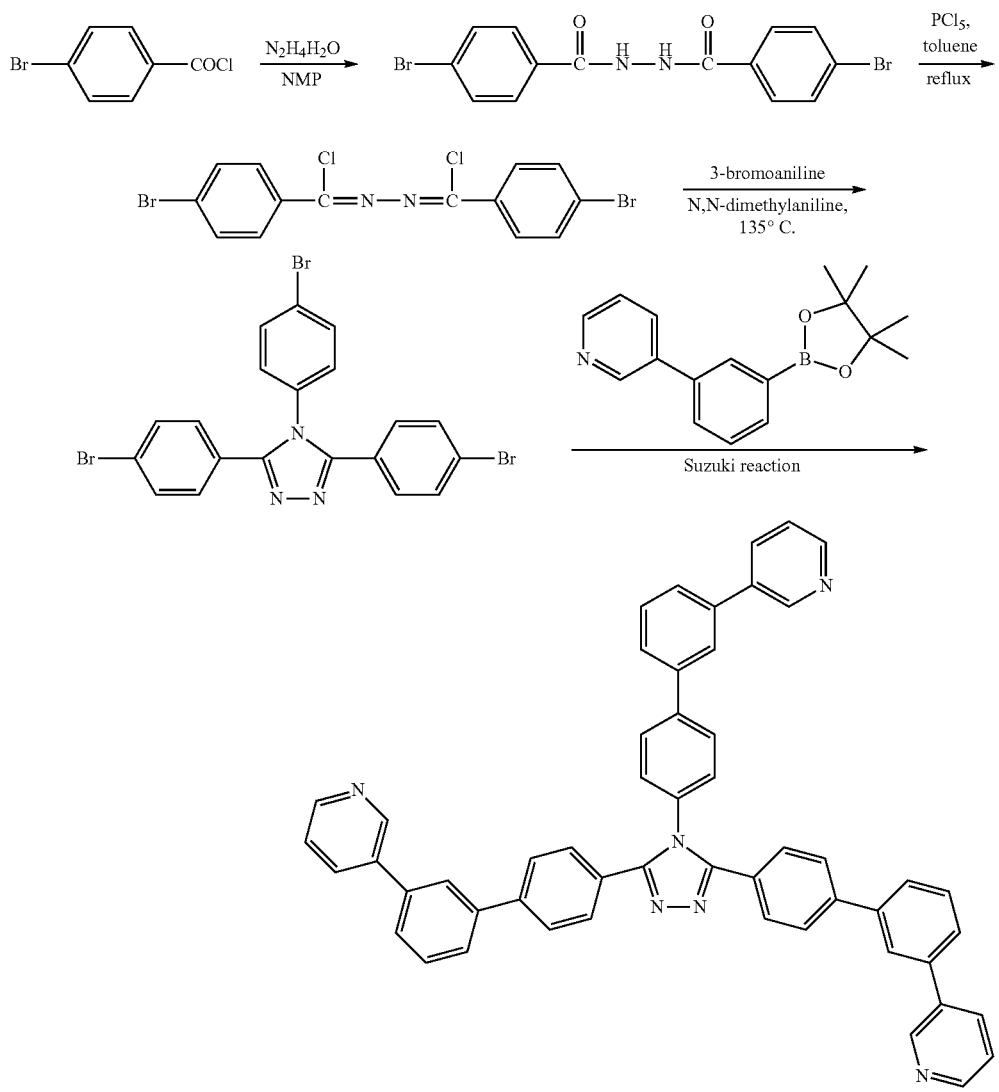

The preparation method thereof is described, as follows:

(1) preparing 3,4,5-tris(4-bromophenyl)-4H-1,2,4-triazole following steps (1) to (3) of example 1

(2) preparing 3-[3-(4,4,5,5-tetramethyl-[1,3,2]-dioxaborolan-2-yl)-phenyl]-pyridine

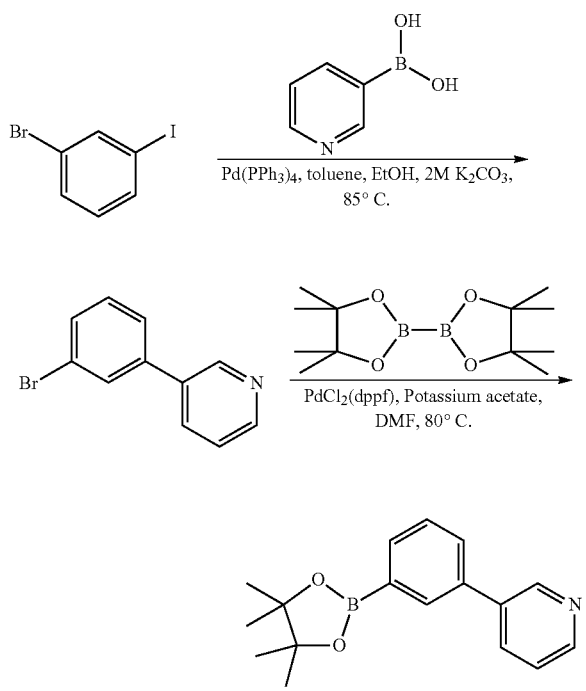

Figure 9:
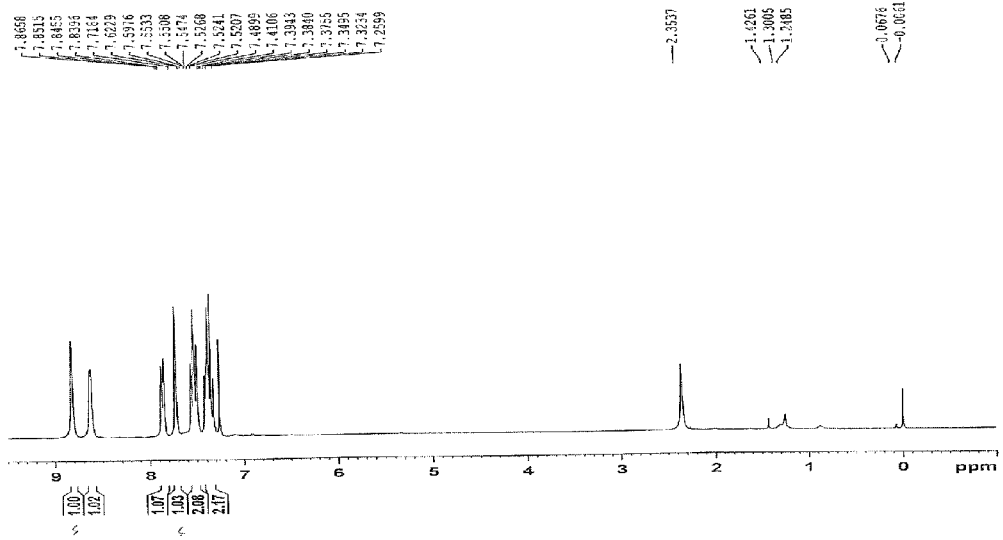
FIG. 9 is a spectrum that characterizes 3-(3-bromo-phenyl)-pyridine.

In the atmosphere of argon, 1-bromo-3-iodo-benzen (11.35 g, 40.1 mmol), 3-pyridylboronic acid (4.87 g, 39.9 mmol), 160 ml toluene, 32 ml ethanol, 32 ml potassium carbonate solution of 2 mol/L and tetrakis(triphenylphosphine)palladium (0.5 g, 0.43 mmol) as a catalyst are loaded into a 500 ml three-neck flask and stirred followed by reacting for 24 hours at a temperature of 85° C. The reaction is quenched by water after being cooled down to the room temperature. Dichloromethane is added to attenuate and separate, and the aqueous phase obtained is extracted by dichloromethane for three times. The organic phase is merged and washed by saturated salt water for three times which is then dried by magnesium sulfate. The reaction system is suction filtrated, and the solvent of the filtrate obtained is removed under reduced pressure. After column separation, 6.65 g light yellow liquid (that is 3-(3-bromo-phenyl)-pyridine) is gained. The yield rate is 71.3% and the spectrum is seen in FIG. 9.

$^1$H NMR (300 MHz, CDCl$_3$, δ, ppm): 8.82 (s, 1H), 8.62 (s, 1H), 7.86 (d, 1H), 7.72 (s, 1H), 7.52 (t, 2H), 7.42-7.32 (m, 2H).

Figure 10:
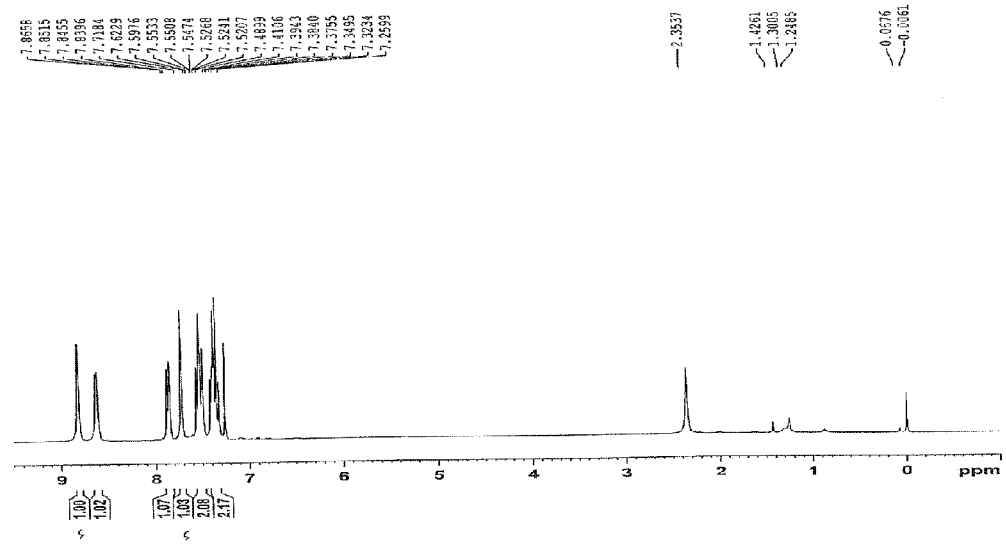
FIG. 10 is a spectrum that characterizes 3-[3-(4,4,5,5-tetramethyl-[1,3,2]-dioxaborolan-2-yl)-phenyl]-pyridine.

In the atmosphere of argon, 3-(3-bromo-phenyl)-pyridine (6.65 g, 28.5 mmol), B(Pin)$_2$ (7.97 g, 31.4 mmol), 100 ml anhydrous N,N-dimethylformamide (DMF), potassium acetate (11.3 g, 115.1 mmol) and PdCl$_2$(dppf) (0.3 g, 0.40 mmol) as a catalyst are loaded into a 250 ml three-neck flask and stirred followed by reacting for 24 hours at a temperature of 80° C. The reaction is quenched by water after being cooled down to the room temperature. Dichloromethane is added to attenuate and separate, and the aqueous phase obtained is extracted by dichloromethane for three times. The organic phase is merged and washed by deionized water for five times which is then dried by magnesium sulfate. The reaction system is suction filtrated, and the solvent of the filtrate obtained is removed under reduced pressure. After column separation, 6.40 g light yellow liquid is gained, that is target product 3-[3-(4,4,5,5-tetramethyl-[1,3,2]-dioxaborolan-2-yl)-phenyl]-pyridine. The yield rate is 80.2% and the spectrum is seen in FIG. 10.

$^1$H NMR (300 MHz, CDCl$_3$, δ, ppm): 8.88 (s, 1H), 8.59 (d, 1H), 8.03 (s, 1H), 7.94 (d, 1H), 7.85 (d, 1H), 7.68 (d, 1H), 7.49 (t, 1H), 7.40-7.34 (m, 1H), 1.37 (s, 12H).

(3) Preparing 3,4,5-tris(4-(3-pyridyl-3-phenyl)-phenyl)-4H-1,2,4-triazole (TPyBnTAZp) Represented by Formula iii

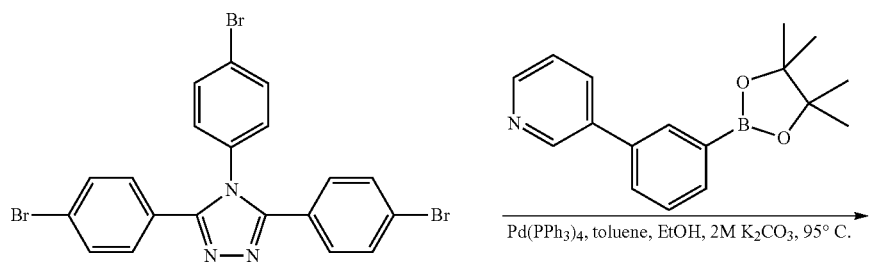

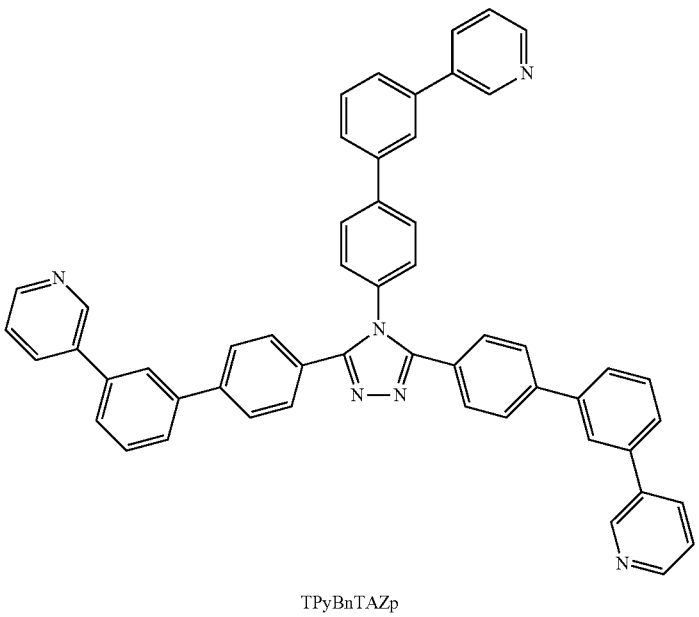

TPyBnTAZp

Figure 11A:
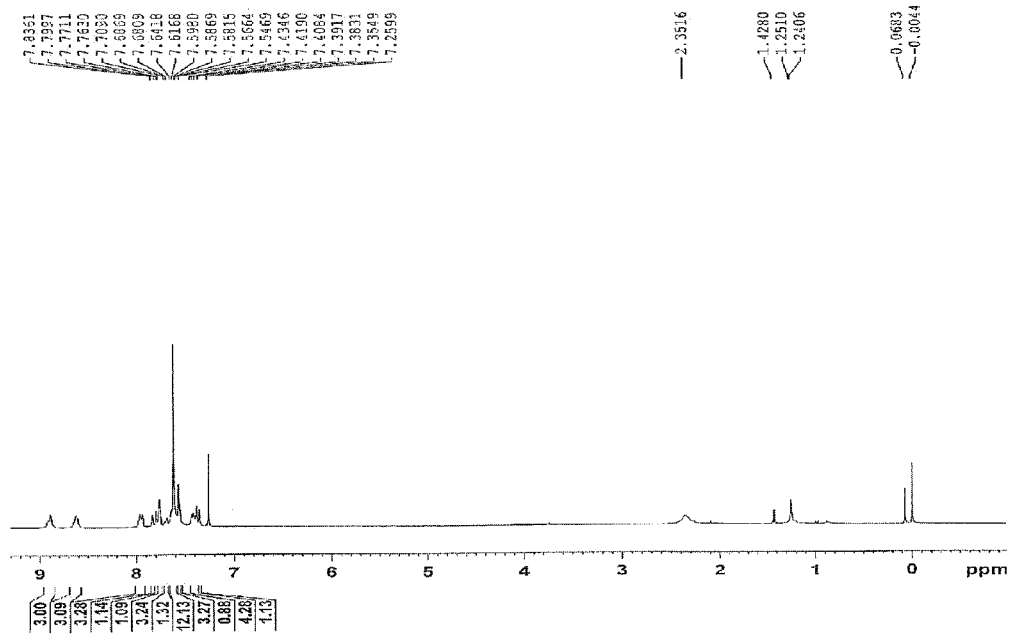
FIGS. 11a and 11b are spectrums that characterize 3,4,5-tris(4-(3-pyridyl-3-phenyl)-phenyl)-4H-1,2,4-triazole (TPyBnTAZp)
Figure 11B:
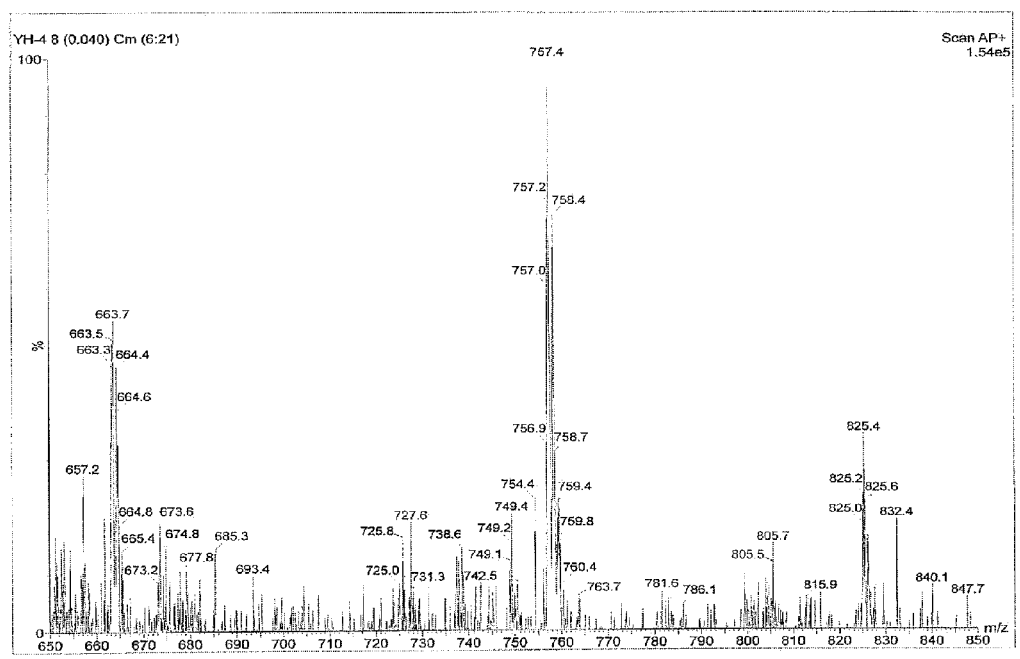

In the atmosphere of argon, 3,4,5-tris(4-bromophenyl)-4H-1,2,4-triazole (0.267 g, 0.5 mmol), 3-[3-(4,4,5,5-tetramethyl-[1,3,2]-dioxaborolan-2-yl)-phenyl]-pyridine (0.45 g, 1.61 mmol), 15 ml toluene, 3 ml ethanol, 3 ml potassium carbonate solution of 2 mol/L and tetrakis(triphenylphosphine)palladium (34 mg, 0.029 mmol) as a catalyst are loaded into a 250 ml three-neck flask and stirred followed by reacting for 24 hours at a temperature of 95° C. The reaction is quenched by water after being cooled down to the room temperature. Dichloromethane is added to attenuate and separate, and the aqueous phase obtained is extracted by dichloromethane for three times. The organic phase is merged and washed by saturated salt water for three times which is then dried by magnesium sulfate. The reaction system is suction filtrated, and the solvent of the filtrate obtained is removed under reduced pressure. After column separation, 0.30 g white solid is gained, that is target product TPyBnTAZp. The yield rate is 76.5% and the spectrum is seen in FIG. 11a and FIG. 11b.

$^1$H NMR (300 MHz, CDCl$_3$, δ, ppm): 8.88 (s, 3H), 8.62 (s, 3H), 7.98-7.92 (m, 3H), 7.84 (s, 1H), 7.80 (s, 1H), 7.76 (s, 3H), 7.72-7.68 (m, 1H), 7.62-7.60 (m, 12H), 7.57 (s, 3H), 7.55 (s, 1H), 7.45-7.38 (m, 4H), 7.35 (s, 1H). Calcd C$_{53}$H$_{36}$N$_6$ 756.9, APCI$^+$-MS (m/z): 757.4 (M$^+$).

EXAMPLE 4

The Preparation of the Micromolecular Electron Transport Material Represented by Formula iv The example provides a micromolecular electron transport material based on pyridine and triazole, which is contained in an electron transfer layer of an organic light-emitting diode or a polymer light-emitting diode, wherein the micromolecular electron transport material is represented by the following formula iv:

formula iv

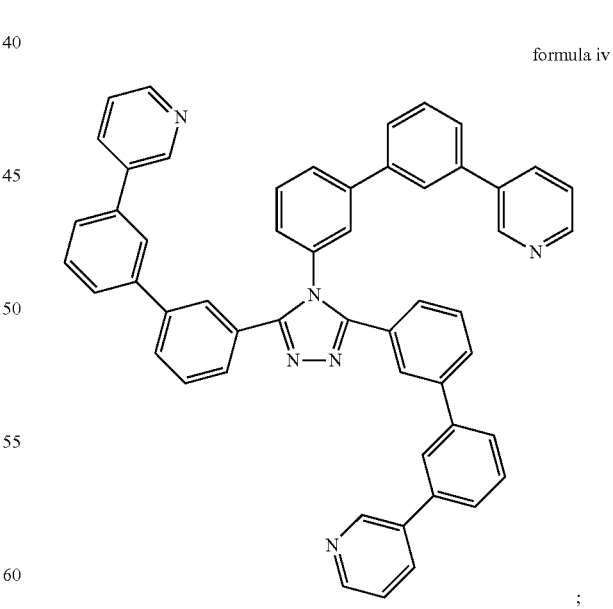

and the synthetic route thereof is as follows.

Figure 12A:
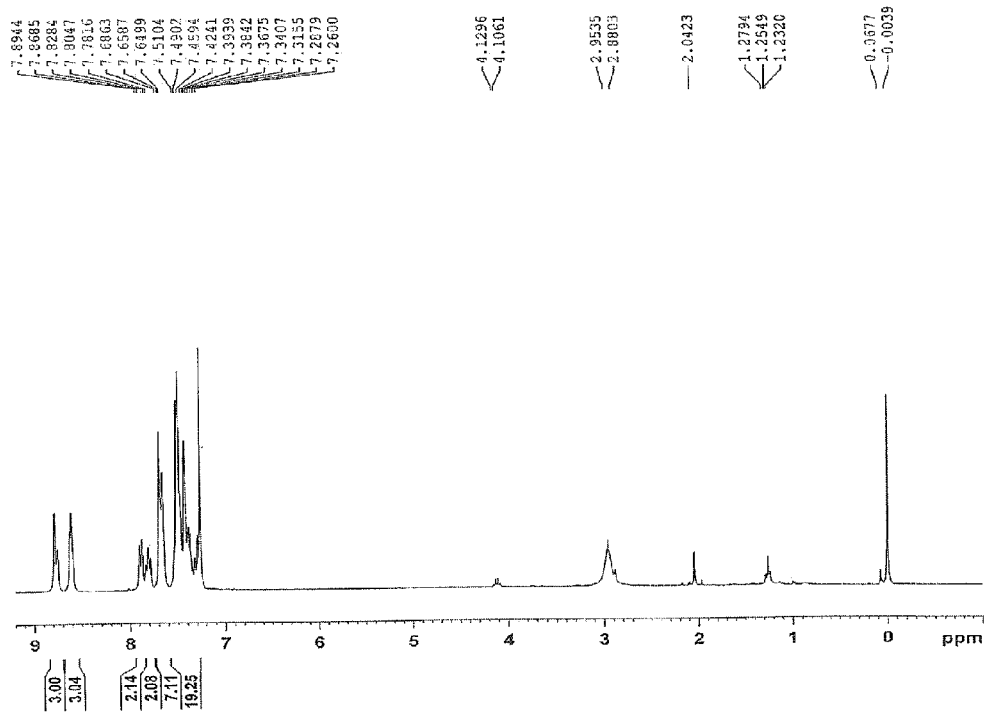
FIGS. 12a to 12c are spectrums that characterize 3,4,5-tris(3-(3-pyridyl-3-phenyl)-phenyl)-4H-1,2,4-triazole (TPyBnTAZm)
Figure 12B:
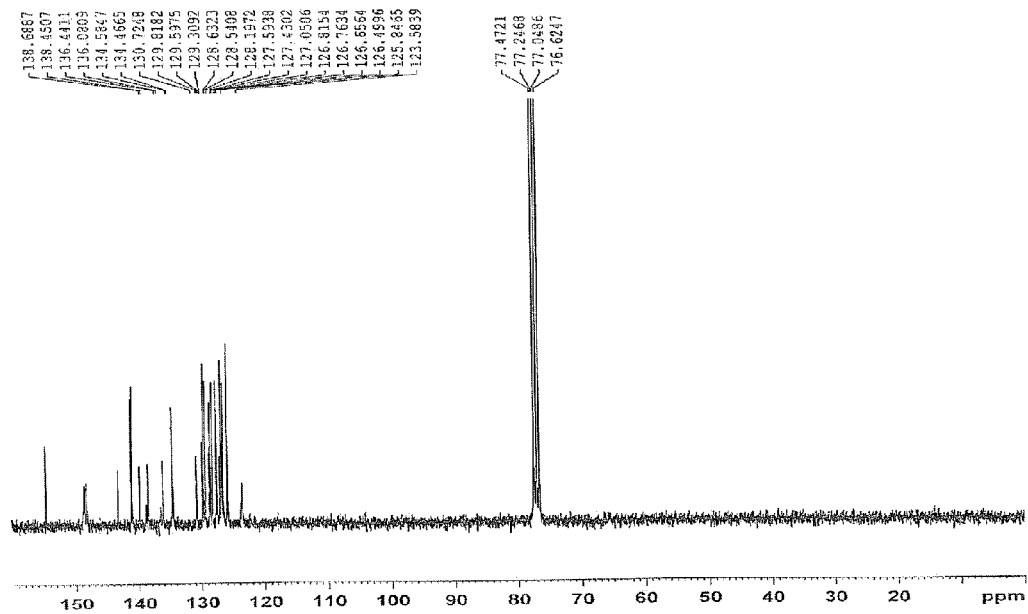
Figure 12C:
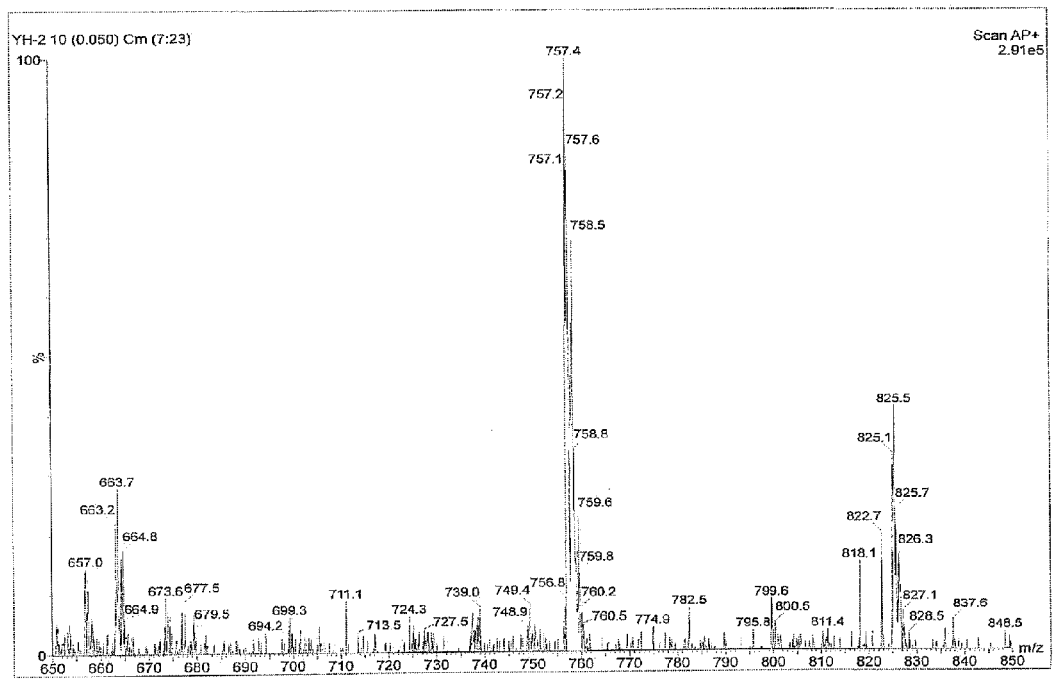

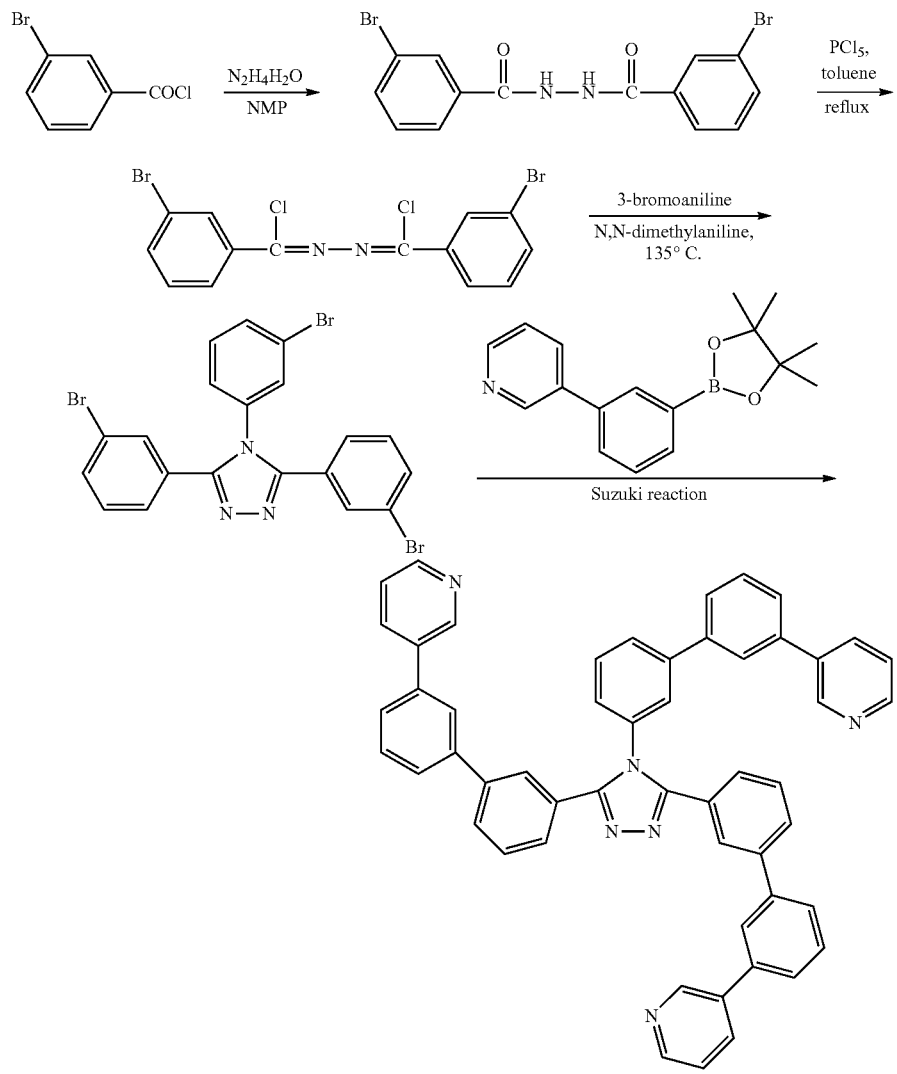
The preparation method thereof is described, as follows:
(1) preparing 3,4,5-tris(3-bromophenyl)-4H-1,2,4-triazole following steps (1) to (3) of example 2.
(2) preparing 3-[3-(4,4,5,5-tetramethyl-[1,3,2]-dioxaborolan-2-yl)-phenyl]-pyridine following steps (2) of example 3.
(3) preparing 3,4,5-tris(3-(3-pyridyl-3-phenyl)-phenyl)-4H-1,2,4-triazole (TPyBnTAZm) represented by formula iv
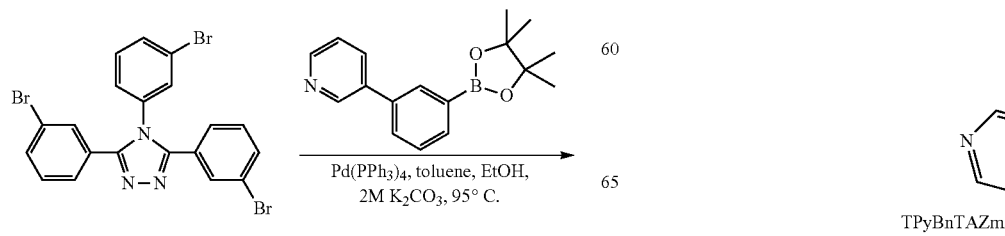
TPyBnTAZm In the atmosphere of argon, 3,4,5-tris(3-bromophenyl)-4H-1,2,4-triazole (2.14 g, 4.0 mmol), 3-[3-(4,4,5,5-tetramethyl-[1,3,2]-dioxaborolan-2-yl)-phenyl]-pyridine (4.43 g, 15.8 mmol), 100 ml toluene, 30 ml ethanol, 30 ml potassium carbonate solution of 2 mol/L and tetrakis (triphenylphosphine) palladium (155 mg, 0.13 mmol) as a catalyst are loaded into a 250 ml three-neck flask and stirred followed by reacting for 24 hours at a temperature of 95° C. The reaction is quenched by water after being cooled down to the room temperature. Dichloromethane is added to attenuate and separate, and the aqueous phase obtained is extracted by dichloromethane for three times. The organic phase is merged and washed by saturated salt water for three times which is then dried by magnesium sulfate. The reaction system is suction filtrated, and the solvent of the filtrate obtained is removed under reduced pressure. After column separation, 2.4 g white solid is gained, that is target product TPyBnTAZm. The yield rate is 79.7% and the spectrum is seen in FIG. 12a to FIG. 12c.

$^1$H NMR (300 MHz, CDCl$_3$, δ, ppm): 8.78 (s, 2H), 8.75 (s, 1H), 8.63-8.57 (m, 3H), 7.88 (d, 2H), 7.85-7.77 (m, 2H), 7.68 (s, 4H), 7.67-7.64 (m, 3H), 7.54-7.45 (m, 11H), 7.43-7.38 (m, 4H), 7.35-7.28 (m, 4H). $^{13}$C NMR (75 MHz, CDCl$_3$, δ, ppm): 154.57, 148.47, 148.14, 143.12, 141.05, 140.86, 139.77, 138.69, 138.45, 136.44, 136.08, 134.58, 134.47, 130.72, 129.82, 129.60, 129.31, 128.63, 128.54, 128.20, 127.59, 127.43, 127.05, 126.82, 126.76, 126.66, 126.50, 125.85, 123.58. Calcd C$_{53}$H$_{36}$N$_6$ 756.9, APCI$^+$-MS (m/z): 757.4 (M$^+$)

EXAMPLE 5

Analysis of the Micromolecular Electron Transport Material of Example 1 to Example 4

(1) Thermoanalysis

Please refer to table 1 which records decomposition temperature and glass transition temperature of the micromolecular electron transport material of example 1 to example 4.

TABLE 1 thermal property of materials

| Sample | Decomposition temperature (T$_d$)/° C. | glass transition temperature (T$_g$)/° C. |
| --- | --- | --- |
| TPyTAZp | 457.7 | — |
| TPyBnTAZp | 497.5 | 107.5 |
| TPyTAZm | 449.5 | 76.8 |
| TPyBnTAZm | 510.3 | 94 |

Figure 13:
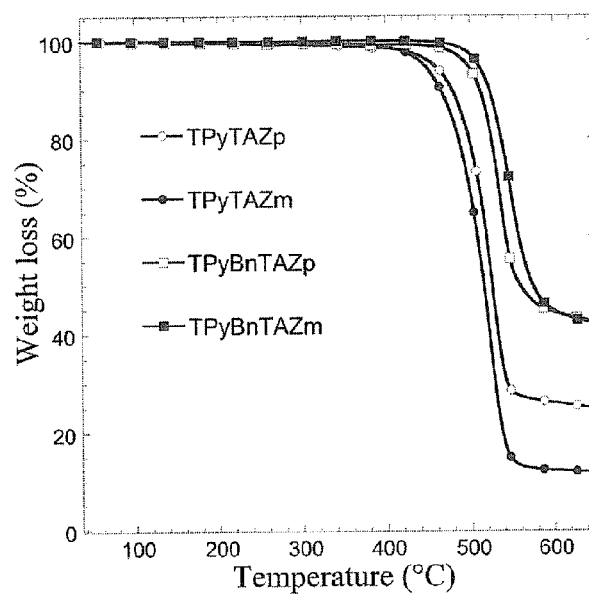
FIG. 13 is a TGA spectrum of the micromolecular electron transport material of the present invention.
Figure 14:
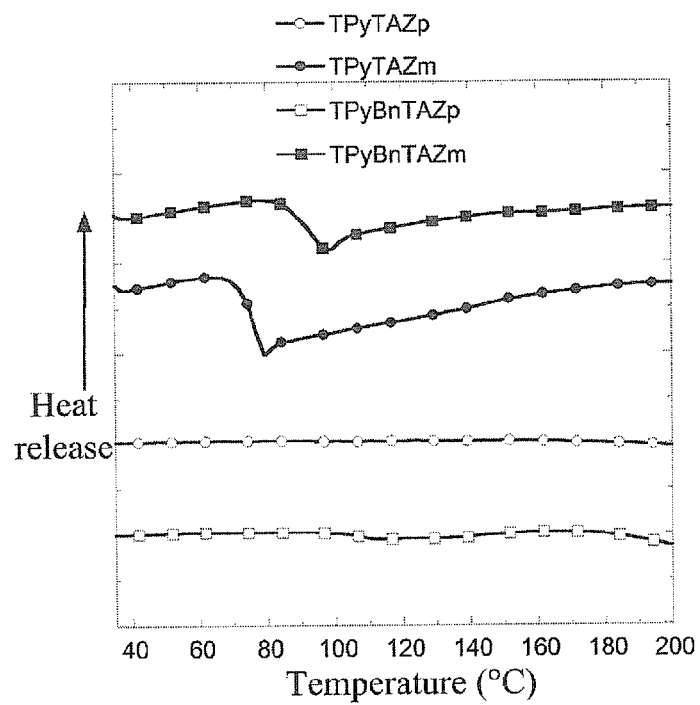
FIG. 14 is a differential scanning calorimetry(DSC) spectrum of the micromolecular electron transport material of the present invention.

It can be concluded from table 1 that the decomposition temperatures of TPyTAZp, TPyBnTAZp, TPyTAZm and TPyBnTAZm are 458° C., 498° C., 446° C. and 510° C., respectively. Further, refer to FIG. 13 which is a TGA spectrum of the micromolecular electron transport material of example 1 to example 4, it is clear that each of the micromolecular electron transport material of example 1 to example 4 performs excellent thermostability.

(2) Analysis of Optical Properties

Figure 15A:
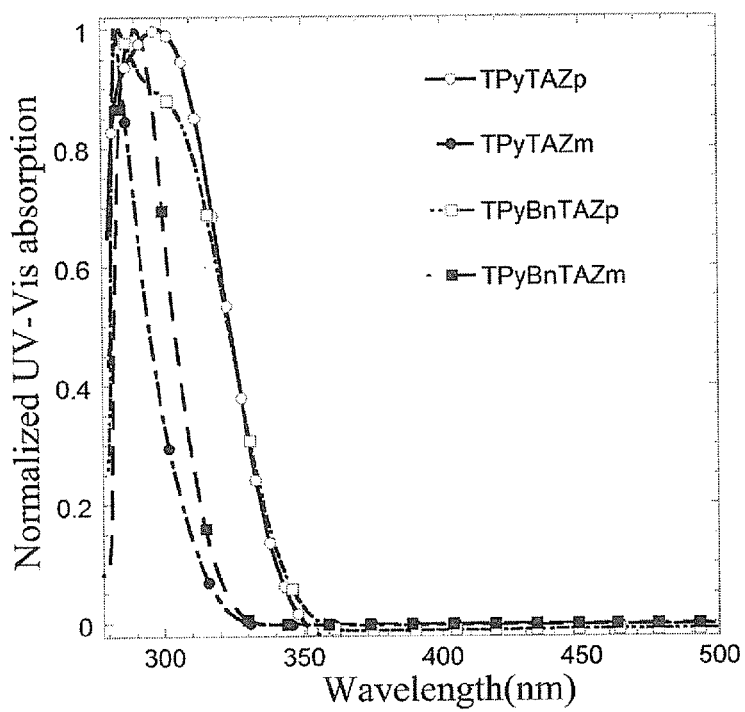
FIGS. 15a and 15b are UV-Vis absorption spectrums of the micromolecular electron transport material of the present invention in toluene solution and in film state, respectively.
Figure 15B:
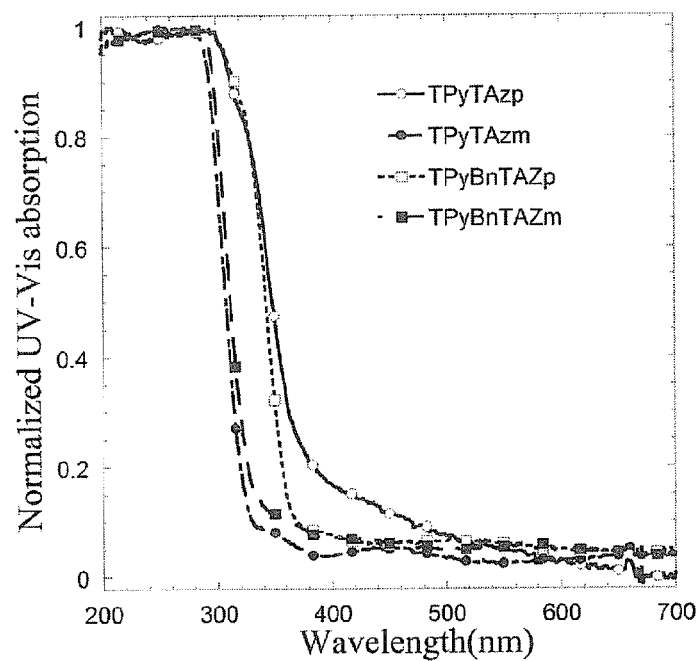
Figure 16A:
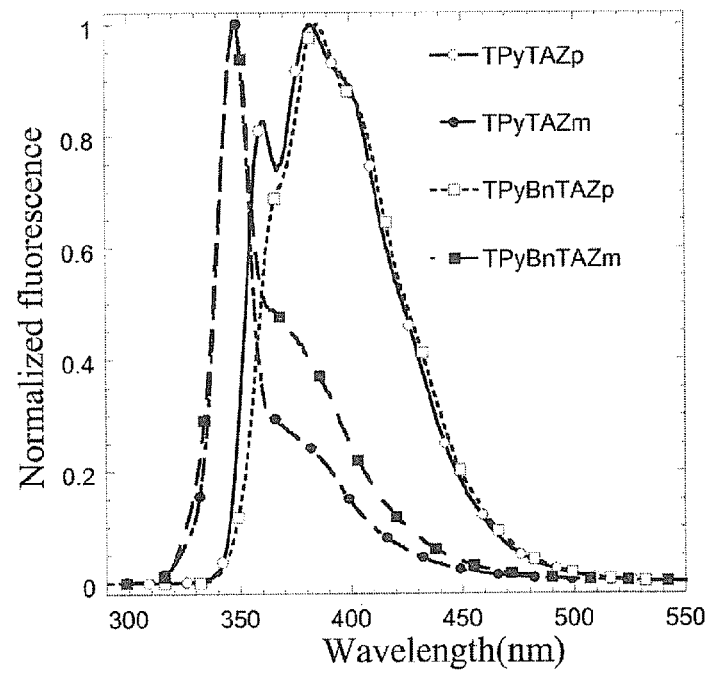
FIGS. 16a and 16b are fluorescence spectrums of the micromolecular electron transport material of the present invention in toluene solution and in film state, respectively.
Figure 16B:
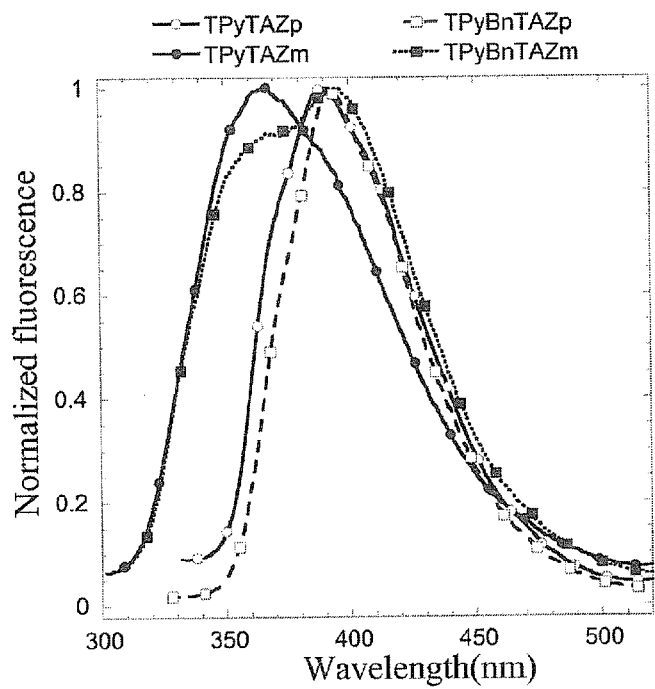

Please refer to FIGS. 15a, 15b, 16a and 16b, wherein FIG. 15a is an UV-Vis absorption spectrums of the micromolecular electron transport material of example 1 to example 4 in toluene solution, FIG. 15b is an UV-Vis absorption spectrums of the micromolecular electron transport material of example 1 to example 4 in film state (right), FIG. 16a is a fluorescence spectrum of the micromolecular electron transport material of example 1 to example 4 in toluene solution, and FIG. 16b is a fluorescence spectrum of the micromolecular electron transport material of example 1 to example 4 in film state.

It is clear in FIG. 15a that, in toluene solution, the TPyTAZp that has pyridine rings attached in peripheral has an absorption peak at 300 nm due to the two molecules at para-position of triazoles, and the conjugation length of molecule is shortened because of the worse conjugacy of benzene rings connecting at meta-position, so that the absorption peak of the TPyTAZp containing pyridyl benzene is blue shift to 285 nm and shows a shoulder peak at 300 nm. Due to the two molecules at meta-position of triazoles, the TPyTAZm that has pyridine rings attached in peripheral has an absorption peak at 283 nm and the TPyBnTAZm that has pyridyl benzene has an absorption peak at 290 nm, which indicates that although the benzene rings that connect at meta-position perform a worse conjugacy, the conjugation length of TPyBnTAZm is increased because there are three more benzene rings contained in TPyBnTAZm than those in TPyTAZm.

It is clear in FIG. 15b that, compared with those in toluene solution, there are no obvious changes in the absorption peak of the micromolecular electron transport material of example 1 to example 4 in film state. However, the absorption ranges of TPyTAZm and TPyBnTAZm are narrower than those of TPyTAZp and TPyBnTAZp in both above conditions.

It is clear in FIG. 16a that, compared with those in the absorption spectrums, the micromolecular electron transport material of example 1 to example 4 shows a red-shift in fluorescence spectrums. In toluene solution, the peaks of fluorescence emission of TPyTAZp and TPyBnTAZp are at 382 nm and 385 nm while those of TPyTAZm and TPyBnTAZm are at 349 nm and 348 nm and perform smaller Stokes Shifts. However, it is obvious that the former have a wider half peak width.

It is clear in FIG. 16b that, compared with those in toluene solution, the fluorescence spectrum of the micromolecular electron transport material of example 1 to example 4 in film state shows a red shift, in which the peaks of fluorescence emission are 390 nm (TPyTAZp), 393 nm (TPyBnTAZp), 367 nm (TPyTAZm) and 391 nm (TPyBnTAZm). Moreover, the spectrum of the TPyBnTAZm is very wide and shows a wide shoulder peak at 350 nm, which may relate to an aggregation of the material in film state.

(3) Electrochemical Properties

Figure 17A:
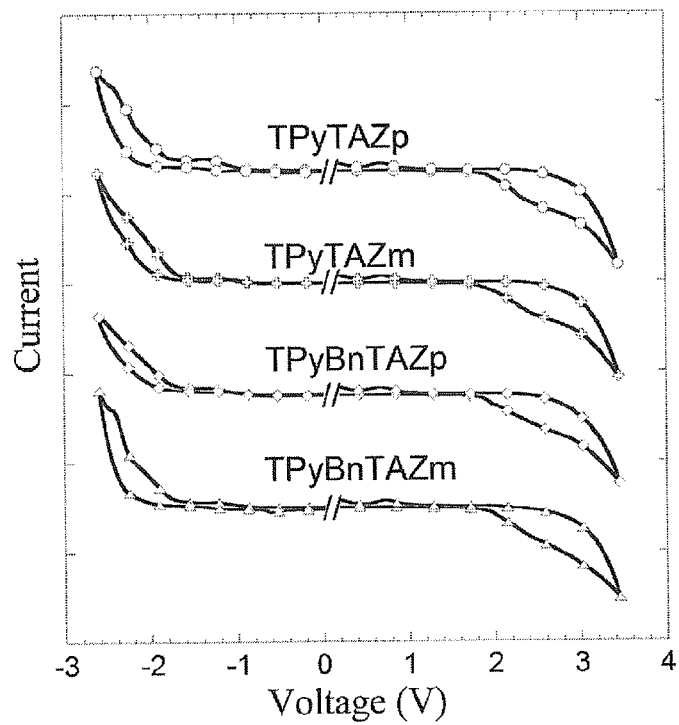
FIG. 17a is a cyclic voltammograms(CV) spectrum of the micromolecular electron transport material of the present invention.
Figure 17B:
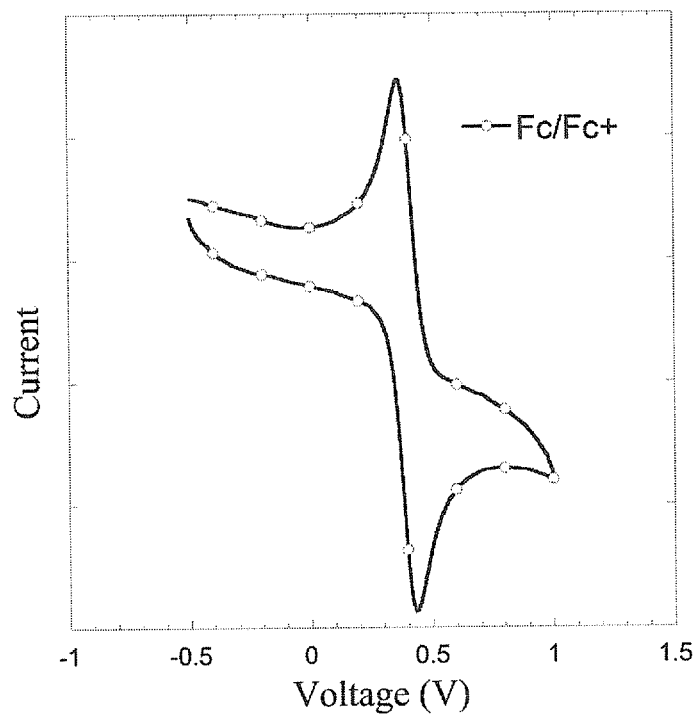
FIG. 17b is a CV spectrum of ferrocene.

The applicant has further measured the electrochemical properties of the micromolecular electron transport material of example 1 to example 4 and the results are shown in FIG. 17a, FIG. 17b and table 2, wherein FIG. 17a is a cyclic voltammograms(CV) spectrum of the micromolecular electron transport material of example 1 to example 4, FIG. 17b is a CV spectrum of ferrocene and table 2 records the optical band gap and electrochemical property of the micromolecular electron transport material of example 1 to example 4.

TABLE 2

| | optical band gap and electrochemical property | | | | | |
|---|---|---|---|---|---|---|
| Material | optical band gap (eV) | oxidation potential (V) | reduction potential (V) | HOMO energy level (eV) | LUMO energy level (eV) | Electrochemical gap (eV) |
| TPyTAZp | 3.32 | 1.87 | −1.67 | −6.27 | −2.73 | 3.54 |
| TPyBnTAZp | 3.42 | 1.82 | −1.62 | −6.22 | −2.78 | 3.44 |
| TPyTAZm | 3.80 | 1.84 | −1.63 | −6.24 | −2.77 | 3.47 |
| TPyBnTAZm | 3.72 | 1.89 | −1.70 | −6.29 | −2.70 | 3.59 |

It is clear in FIG. 17a, FIG. 17b and table 2 that the potential corresponding to an oxidation peak of ferrocene is 0.43V and the potential corresponding to a reduction peak is 0.36V, and the median of the above two is 0.40V. HOMO energy level=−e(oxidation potential+4.40)V and LUMO energy level=−e(reduction potential+4.40)V when ferrocene is used as an internal standard.

EXAMPLE 6

Figure 18:
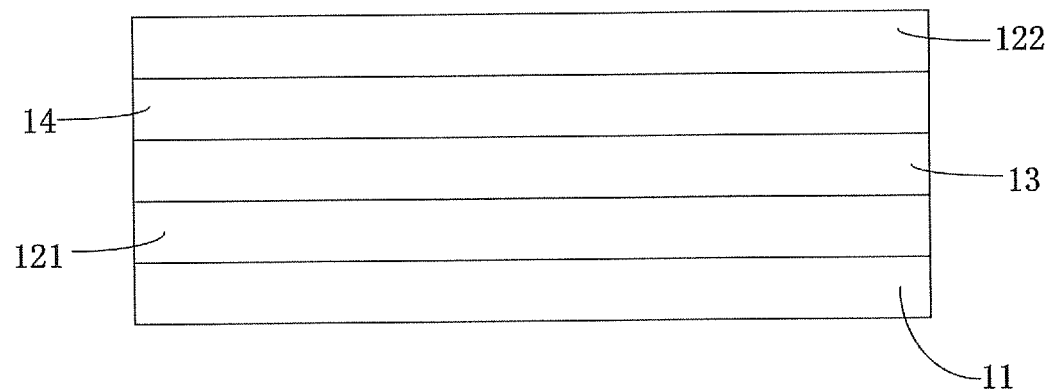
FIG. 18 is a structure schematic of an organic light-emitting diode of one embodiment of the present invention; wherein 10—an organic light-emitting diode of one embodiment of the present invention.

The Application of the Micromolecular Electron Transport Material of Example 1 to Example 4 in Organic Light Emitting Diodes Refer now to FIG. 18, a structure schematic of the organic light-emitting diode provided in the present embodiment. In the present embodiment, the organic light-emitting diode 10 comprises: a substrate 11, a first electrode 121, a second electrode 122 that faces the first electrode 121, a light-emitting layer 13 that is sandwiched between the first electrode 121 and the second electrode 122, and an electron transfer layer 14 that is sandwiched between the light-emitting layer 13 and the second electrode 122. The electron transfer layer 14 contains the micromolecular electron transport material of example 1 to example 4. The substrate is a transparent substrate. It will be appreciated that the micromolecular electron transport material of example 1 to example 4 can be applied to any known organic light-emitting diodes and is not limited in the organic light-emitting diode provided in the present embodiment.

Compared with the existing data and technology, the advantages and positive effects of the present invention are listed as follows:

(1) the preparation method of the micromolecular electron transport material containing pyridine and triazole of the present invention has fewer synthetic steps and is easy to carry out purification, which is conducive to industrial application;

(2) the micromolecular electron transport material containing pyridine and triazole of the present invention has better solubility, film-forming property and shape stability of film;

(3) the micromolecular electron transport material containing pyridine and triazole of the present invention has strong electrophilicity, low LUMU energy level and low energy barrier of electron injection due to the contained triazoles and pyridine rings; and (4) in the micromolecular electron transport material containing pyridine and triazole of the present invention, the pyridine rings and triazoles are connected by meta-benzene that performs poorer conjugation, which may maintain a higher triplet energy level of the materials effectually to block the migration of triplet excitons into the electron transfer layer.

The present invention has been described with relative embodiments which are examples of the present invention only. It should be noted that the embodiments disclosed are not the limit of the scope of the present invention. Conversely, modifications to the scope and the spirit of the claims, as well as the equal of the claims, are within the scope of the present invention.

What is claimed is:

1. A micromolecular electron transport material based on pyridine and triazole, contained in an electron transfer layer of an organic light-emitting diode or a polymer light-emitting diode, wherein the micromolecular electron transport material is represented by the following formula I:

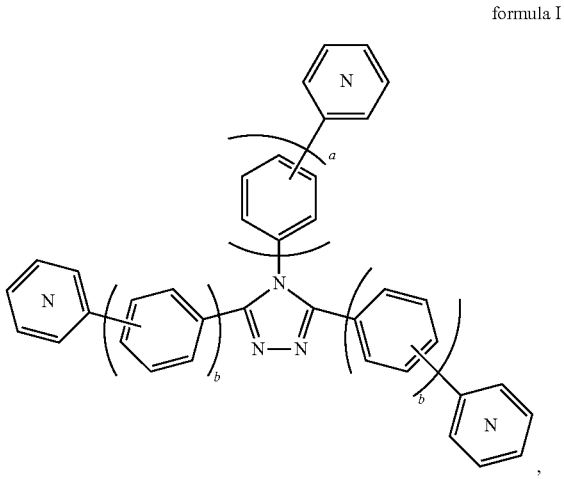

formula I wherein a and b are natural numbers greater than or equal to 1;

N is in ortho-, meta- or para-position of the pyridine ring in formula I; and benzene rings in formula I are connected at the ortho-, meta- or para-positions.

2. The micromolecular electron transport material according to claim 1, wherein the micromolecular electron transport material is represented by the following formula i:

formula i

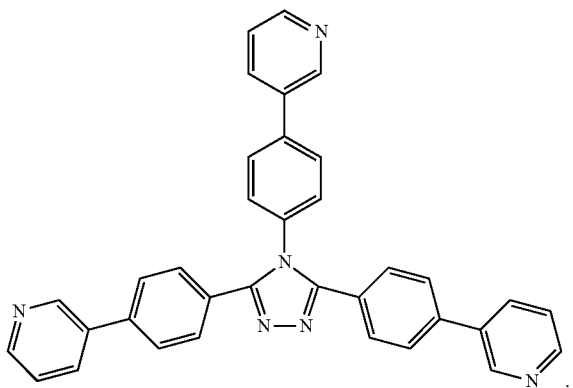

3. The micromolecular electron transport material according to claim 1, wherein the micromolecular electron transport material is represented by the following formula ii:

formula ii

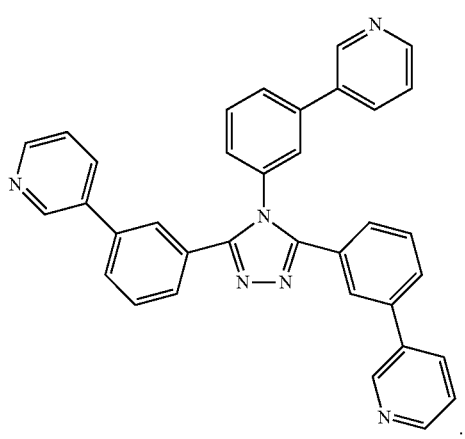

4. The micromolecular electron transport material according to claim 1, wherein the micromolecular electron transport material is represented by the following formula iii:

formula iii

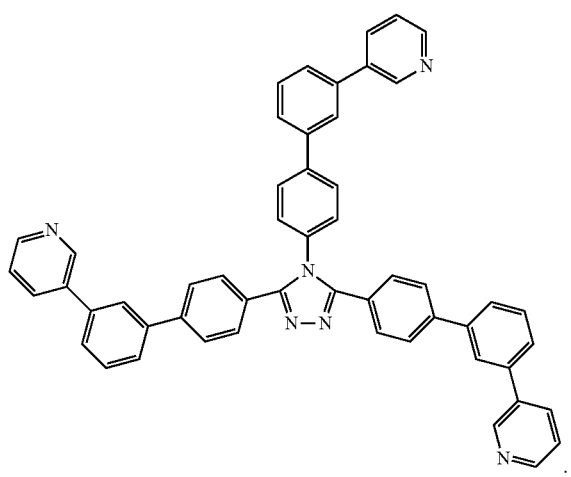

5. The micromolecular electron transport material according to claim 1, wherein the micromolecular electron transport material is represented by the following formula iv:

formula iv

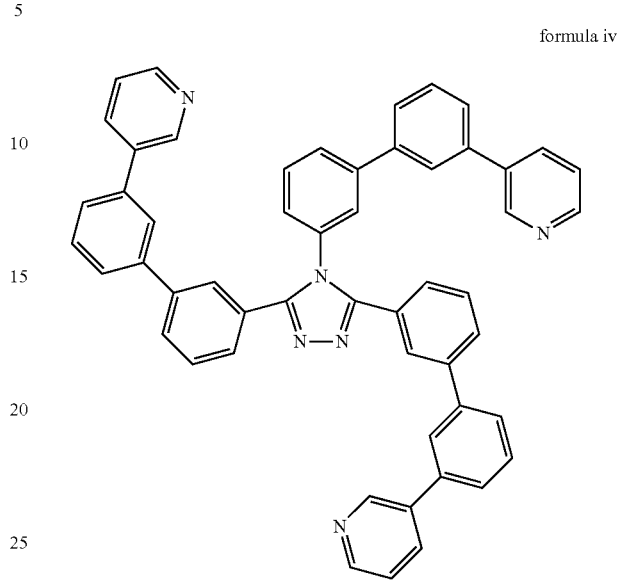

6. A preparation method of the micromolecular electron transport material based on pyridine and triazole according to claim 1, wherein the method comprises the following steps of:
 (1) reacting a starting material A with hydrazine hydrate under the room temperature with N-methyl pyrrolidone as a solvent to synthesize product 1;
 (2) reacting the product 1 with phosphorus pentachloride under reflux with toluene as a solvent to synthesize product 2;
 (3) reacting the product 2 with N,N-dimethylaniline and a reactant B at a temperature of 135° C. to synthesize product 3; and
 (4) carrying out a Suzuki reaction occurs between the product 3 and a reactant C at a temperature of 95° C. to synthesize a target product;
 wherein the starting material A is selected from 4-bromobenzoyl chloride or 3-bromobenzoyl chloride, the reactant B is selected from 3-bromoaniline or 4-bromoaniline, and the reactant C is selected from 3-Pyridylboronic acid or 3-[3-(4,4,5,5-tetramethyl[1,3,2]dioxaborolan-2-yl)-phenyl]-pyridine.

7. An organic light-emitting diode, wherein the organic light-emitting diode comprises: a substrate, a first electrode, a second electrode that faces the first electrode, a light-emitting layer that is sandwiched between the first electrode and the second electrode, and an electron transfer layer that is sandwiched between the light-emitting layer and the second electrode; wherein the electron transfer layer contains the micromolecular electron transport material based on pyridine and triazole according to claim 1.

8. The organic light-emitting diode according to claim 7, wherein the substrate is a transparent substrate.

9. The organic light-emitting diode according to claim 7, wherein the micromolecular electron transport material is represented by the following formula i:

formula i

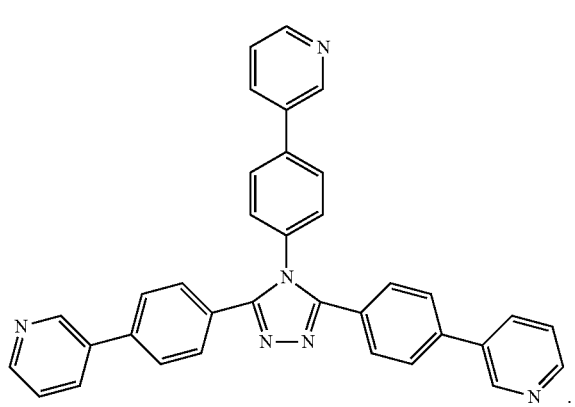

10. The organic light-emitting diode according to claim 7, wherein the intermolecular electron transport material is represented by the following formula ii:

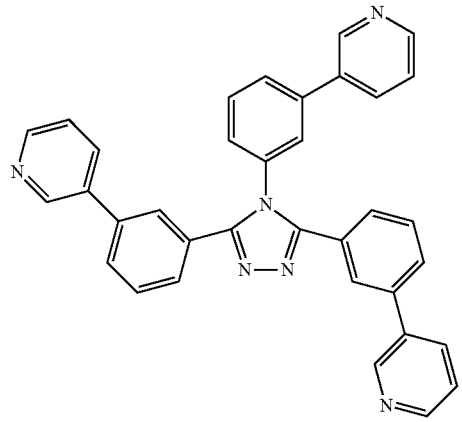

formula ii

11. The organic light-emitting diode according to claim 7, wherein the micromolecular electron transport material is represented by the following formula iii:

formula iii

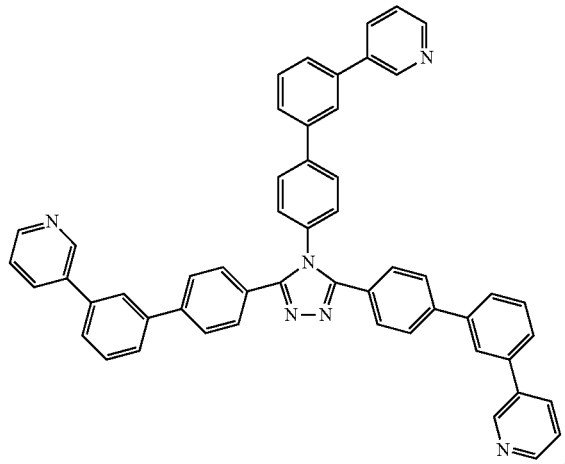

12. The organic light-emitting diode according to claim 7, wherein the micromolecular electron transport material is represented by the following formula iv:

formula iv

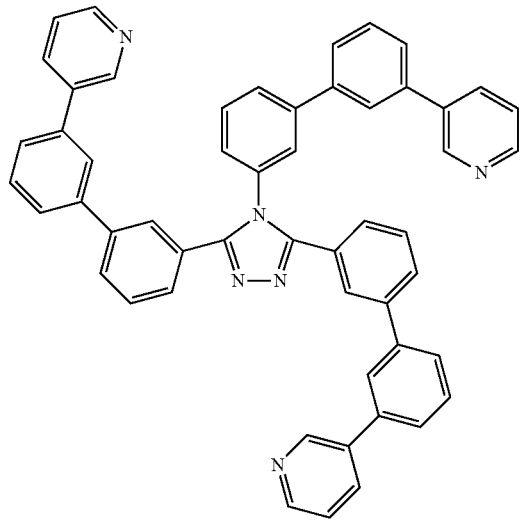

* * * * *